(12) United States Patent
Freyne et al.

(10) Patent No.: US 8,778,920 B2
(45) Date of Patent: *Jul. 15, 2014

(54) 3-CYANO-QUINOLINE DERIVATIVES WITH ANTIPROLIFERATIVE ACTIVITY

(75) Inventors: Eddy Jean Edgard Freyne, Rumst (BE); Peter Jacobus Johannes Antonius Buijnsters, JX Breda (NL); Kristof Van Emelem, Sint-Niklaas (BE); Werner Constant Johan Embrechts, Oud-Turnhout (BE); Timothy Pietro Suren Perera, Geel (BE)

(73) Assignee: Janssen Pharmaceutica NV, Beerse (BE)

( * ) Notice: Subject to any disclaimer, the term of this patent is extended or adjusted under 35 U.S.C. 154(b) by 1216 days.

This patent is subject to a terminal disclaimer.

(21) Appl. No.: 12/624,708

(22) Filed: Nov. 24, 2009

(65) Prior Publication Data

US 2010/0069424 A1 Mar. 18, 2010

Related U.S. Application Data

(62) Division of application No. 10/596,509, filed as application No. PCT/EP2004/053497 on Dec. 15, 2004, now Pat. No. 7,655,642.

(51) Int. Cl.
*A61K 31/33* (2006.01)
*C07D 487/00* (2006.01)
*C07D 491/08* (2006.01)

(52) U.S. Cl.
USPC .......................... 514/183; 540/456; 540/477

(58) Field of Classification Search
None
See application file for complete search history.

(56) References Cited

U.S. PATENT DOCUMENTS

| 6,002,008 | A | 12/1999 | Wissner et al. |
| 6,288,082 | B1 | 9/2001 | Wissner et al. |
| 7,655,642 | B2 | 2/2010 | Freyne et al. |

FOREIGN PATENT DOCUMENTS

| WO | WO 98/43960 A1 | 10/1998 |
| WO | WO 00/18761 A1 | 4/2000 |
| WO | WO 03/082290 A1 | 10/2003 |
| WO | WO 2004/105765 A1 | 12/2004 |

OTHER PUBLICATIONS

Brown, B., et al. "FlashPlate Technology—Principles and Characteristics of Flashplate Scintillation Counting", High throughput Screening, The discovery of Bioactive Substances, edited by John P. Devlin, Ph.D., Dekker, Inc., New York pp. 317-328.
Burke, T., "Protein-Tyrosine Kinase Inhibitors", Drugs of the Future (1992) vol. 17(2) pp. 119-131.

Davies, S., et al. "Specificity and Mechanism of Action of Some Commonly Used Protein Kinase Inhibitors", Biochemistry Journal (2000) vol. 351, pp. 95-105.

(Continued)

*Primary Examiner* — Noble Jarrell

(57) ABSTRACT

The present invention concerns the compounds of formula

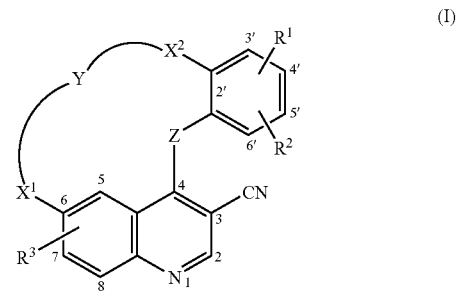

(I)

the N-oxide forms, the pharmaceutically acceptable addition salts and the stereochemically isomeric forms thereof, wherein Z represents NH;

Y represents —$C_{3-9}$alkyl-, —$C_{1-5}$alkyl-$NR^{12}$—$C_{1-5}$alkyl-, —$C_{1-6}$alkyl-NH—CO— or —CO—NH—$C_{1-6}$alkyl-;

$X^1$ represents —O—;

$X^2$ represents a direct bond, —$NR^{11}$—$C_{1-2}$alkyl-, —$NR^{11}$—$CH_2$—, —$C_{1-2}$alkyl-, —O—$C_{1-2}$alkyl, —O— or —O—$CH_2$—;

$R^1$ represents hydrogen or halo;

$R^2$ represents hydrogen, cyano, halo, hydroxycarbonyl-, $C_{1-4}$alkyloxycarbonyl-, $Het^{16}$-carbonyl- or $Ar^5$;

$R^3$ represents hydrogen, hydroxy, $C_{1-4}$alkyloxy-, $Ar^4$—$C_{1-4}$alkyloxy or $R^3$ represents $C_{1-4}$alkyloxy substituted with one or where possible two or more substituents selected from $C_{1-4}$alkyloxy- or $Het^2$-;

$R^{10}$ represents hydrogen;

$R^{11}$ represents hydrogen, $C_{1-4}$alkyl- or $C_{1-4}$alkyl-oxy-carbonyl-;

$R^{12}$ represents $Het^{14}$-$C_{1-4}$alkyl, in particular morpholinyl-$C_{1-4}$alkyl;

$Het^2$ represents a heterocycle selected from morpholinyl or piperidinyl optionally substituted with $C_{1-4}$alkyl-, preferably methyl;

$Het^{14}$ represents morpholinyl;

$Het^{16}$ represents a heterocycle selected from morpholinyl or pyrrolidinyl;

$Ar^4$ represents phenyl;

$Ar^5$ represents phenyl optionally substituted with cyano.

6 Claims, No Drawings

(56) References Cited

OTHER PUBLICATIONS

Delia, T.,Fused Pyrimidines, Part Four, Miscellaneous Fused Pyrimidines: Chapter Vi-Pyrimidotriaznes, Heterocyclic Compounds, John Wiley 7 Sons, Inc., Interscience Publication, pp. 261-204.
Druker, B, et al. "Lessons Learned From the Development of An Abl tyrosine Kinase Inhibitor for Chronic Myetogenous Leukemia", the Journal of Clinical Investigation, (2000) vol. 5, No. 1, pp. 3-7.
Elder, J., et al. "Overexpressin of Transforming Growth Factor α in Psoriatic Epidermis", Science (1989) vol. 243, pp. 811-814.
Gennaro Remington's Pharmaceutical Sciences, 19th ed., Mack Publishing Company, Part 8: Pharmaceutical Preparations and Their Manufacture (1990).
Greene "Protective Groups in Organic Synthesis", 3nd Ed., Wiley Interscience (1991).
Hennequin, "Novel-4-Anilinoquinazolines with C-7 Basic Side Chains: Design and Structure Activity Relationship of a Series of Potent, Orally Active, VEGF Receptor Tyrosine Kinase Inhibitors", Journal of Medicinal Chemistry, Mar. 14, 2002, pp. 1300-1312, vol. 45, No. 6, American Chemical Society, Washington, US XP002256124.
Morin, M., "From Oncogene to Drug: Development of Small Molecule Tyrosine Kinase Inhibitors as Anti-Tumor and Anti-Angiogenic Agents", Oncogene (2000) pp. 6574-6583, vol. 19.
Nagamatsu, M., Syntheses of 3-Substituted 1-Methyl-6-Phenylpyrimido[5,5-e]- 1,2-4-triazine-5,7(1H,6H)-diones (6-Phenyl Analogs of Toxoflavin) and Their 4-Oxides and Evaluation of Antimicrobial Activity of Toxoflavins and Their Analogs, Chem. Pharmaceutical Bulletin (1993) pp. 362-368, vol. 41, No. 2.
Nagamatsu, M., "General Syntheses of 1-Alkytoxoflavin and 8-Alkyfervenulin Derivatives of Biological Significance by the Regioselective Alkylation of Reumycin Derivatives and the Rates of Transalkylation From 1-Alkytoxoflavins into Nucleophiles", J. Chemical Society, Perkin Trtnas. 1 (2001) pp. 130-137.
Palmer, D., et al. "Tyrosine Kinase Inhibitors 11 Soluble Analogs of Pyrrolo-and Pyrazoloquinazolines as Epidermal Growth Factor Receptor Inhibitors: Synthesis, Biological Evaluation, and Modeling of the Mode of Binding", Journal of Mediincial Chemistry (1997) pp. 1519-1529, vol. 40, No. 10, American Chemical Society, Washington, US XP002094613.
Rusnak, D., "The Characterization of Novel, Dual Erbb-2/EGFR, Tyrosine Kinase Inhibitors: Potential Therapy for Cancer", Cancer Research (2001), vol. 61, Issue 19, pp. 7196-7203.
Shawver, "Smart Drugs: Tyrosine Kinase Inhibitors in Cancer Therapy", Cancer Cells (2002) pp. 117-123, vol. 1.
Wissner, "4-Anlino-6,7-diakoxyquinoline-3-carbonitrile Inhibitor of Epidermal Growth Factor Receptor Kinase and Their Bioisoteric Relationsp to the 4-Anilino-6,7-Dialkyoxquinazoline Inhibitors", Journal of Medicinal Chemistry, (2000) pp. 3244-3256, vol. 43, No. 17, American Chemical society, Washington, US.
Whitley, B., et al., "Rho-kinase, P13K and p38 signal pathways regulate ovarian cancer cell (SKOV-3) migration and invasion", Proceedings of the American Association of Cancer Research, (2004), vol. 45, Abstract #4918.
Psoriasis,"National Library of Medicine—Medical Subject Headings 2008 MeSH", http://www.nlm.nih.gov/cgi/mesh/2008/MB_cgi, accessed Nov. 21, 2008.
PCT International Search Report for corresponding Application No. PCT/EP2004/053497 mailed Apr. 12, 2005.

3-CYANO-QUINOLINE DERIVATIVES WITH ANTIPROLIFERATIVE ACTIVITY

CROSS REFERENCE TO RELATED APPLICATIONS

This application is a divisional application of U.S. application Ser. No. 10/596,509, filed Jun. 15, 2006, now issued as U.S. Pat. No. 7,655,642, which is the national stage of PCT Application No. PCT/EP04/053497, filed Dec. 15, 2004, which application claims priority from PCT Patent Application No. PCT/EP03/051059, filed Dec. 18, 2003, the entire disclosure of which is hereby incorporated in its entirety.

This invention relates to quinoline derived macrocycles that have been found to possess anti-proliferative activity, such as anti-cancer activity and are accordingly useful in methods of treatment of the human or animal body, for example in the manufacture of medicaments for use in hyper proliferative disorders such as atherosclerosis, restenosis and cancer. The invention also relates to processes for the manufacture of said quinoline derivatives, to pharmaceutical compositions containing them and to their use in the manufacture of medicaments of use in the production of anti-proliferative effect.

In particular, the compounds of the present invention were found to inhibit tyrosine kinase enzymes, also called tyrosine kinases. Tyrosine kinases are a class of enzymes, which catalyse the transfer of the terminal phosphate of adenosine triphosphate to the phenolic hydroxyl group of a tyrosine residue present in the target protein. It is known, that several oncogenes, involved in the transformation of a cell into a malignant tumour cell, encode tyrosine kinase enzymes including certain growth factor receptors such as EGF, FGF, IGF-1R, IR, PDGF and VEGF. This family of receptor tyrosine kinases and in particular the EGF family of receptor tyrosine kinases, hereinafter also referred to as EGFR receptor or EGF type receptor tyrosine kinases, are frequently present in common human cancers such as breast cancer, non-small cell lung cancers including adenocarcinomas and squamous cell cancer of the lung, bladder cancer, oesophageal cancer, gastrointestinal cancer such as colon, rectal or stomach cancer, cancer of the prostate, leukaemia and ovarian, bronchial or pancreatic cancer, which are examples of cell proliferation related disorders.

Accordingly, it has been recognised that the selective inhibition of tyrosine kinases will be of value in the treatment of cell proliferation related disorders. Support for this view is provided by the development of Herceptin® (Trastuzumab) and Gleevec™ (imatinib mesylate) the first examples of target based cancer drugs. Herceptin® (Trastuzumab) is targeted against Her2/neu, a receptor tyrosine kinase found to be amplified up to 100-fold in about 30% of patients with invasive breast cancer. In clinical trials Herceptin® (Trastuzumab) proved to have anti-tumour activity against breast cancer (Review by L. K. Shawer et al, "Smart Drugs: Tyrosine kinase inhibitors in cancer therapy", 2002, Cancer Cell Vol. 1, 117), and accordingly provided the proof of principle for therapy targeted to receptor tyrosine kinases. The second example, Gleevec™ (imatinib mesylate), is targeted against the abelson tyrosine kinase (BcR-Abl), a constitutively active cytoplasmic tyrosine kinase present in virtually all patients with chronic myelogenous leukaemia (CML) and 15% to 30% of adult patients with acute lymphoblastic leukaemia. In clinical trials Gleevec™ (imatinib mesylate) showed a spectacular efficacy with minimal side effects that led to an approval within 3 months of submission. The speed of passage of this agent through clinical trials and regulatory review has become a case study in rapid drug development (Drucker B. J. & Lydon N., "Lessons learned from the development of an Abl tyrosine kinase inhibitor for chronic myelogenous leukaemia.", 2000, J. Clin. Invest. 105, 3).

Further support is given by the demonstration that EGF receptor tyrosine kinase inhibitors, specifically attenuates the growth in athymic nude mice of transplanted carcinomas such as human mammary carcinoma or human squamous cell carcinoma (Review by T. R. Burke Jr., Drugs of the Future, 1992, 17, 119). As a consequence, there has been considerable interest in the development of drugs to treat different cancers that target the EGFR receptor. For example, several antibodies that bind to the extra-cellular domain of EGFR are undergoing clinical trials, including Erbitux™ (also called C225, Cetuximab), which was developed by Imclone Systems and is in Phase III clinical trials for the treatment of several cancers. Also, several promising orally active drugs that are potent and relatively specific inhibitors of the EGFR tyrosine kinase are now well advanced in clinical trials. The AstraZeneca compound ZD1839, which is now called IRESSA® and approved for the treatment of advanced non-small-cell lung cancer, and the OSI/Genentech/Roche compound OSI-774, which is now called Tarceva™ (erlotinib), have shown marked efficacy against several cancers in human clinical trials (Morin M. J., "From oncogene to drug: development of small molecule tyrosine kinase inhibitors as anti-tumour and anti-angiogenic agents, 2000, Oncogene 19, 6574).

In addition to the above, EGF receptor tyrosine kinases has been shown to be implicated in non-malignant proliferative disorders such as psoriasis (elder et al., Science, 1989, 243; 811). It is therefore expected that inhibitors of EGF type receptor tyrosine kinases will be useful in the treatment of non-malignant diseases of excessive cellular proliferation such as psoriasis, benign prostatic hypertrophy, atherosclerosis and restenosis.

It is disclosed in U.S. Pat. Nos. 6,288,082 and 6,002,008, in the International Patent Applications WO 98/43960 and WO 00/018761 and in J. Med. Chem., 2000, 43(17), 3244 that certain 4-anilino-3-cyanoquinolines may be useful as inhibitors of tyrosine kinase and in particular of the EGF type receptor tyrosine kinases. Unexpectedly it was found that 3-cyanoquinoline derivatives of the present formula (I) that are different in structure show to have tyrosine kinase inhibitory activity.

It is accordingly an object of the present invention to provide further tyrosine kinase inhibitors useful in the manufacture of medicaments in the treatment of cell proliferative related disorders.

This invention concerns compounds of formula (I)

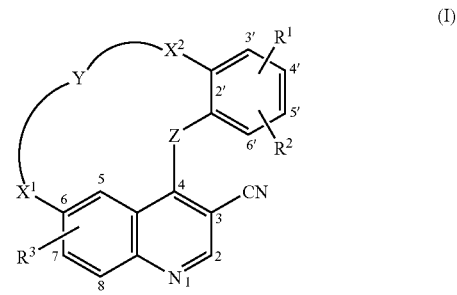

the N-oxide forms, the pharmaceutically acceptable addition salts and the stereochemically isomeric forms thereof, wherein Z represents O, NH or S;

Y represents —$C_{3-9}$alkyl-, —$C_{3-9}$alkenyl-, —$C_{1-5}$alkyl-oxy-$C_{1-5}$alkyl-, —$C_{1-5}$alkyl-NR$^{12}$—$C_{1-5}$alkyl-, —$C_{1-5}$alkyl-NR$^{13}$—CO—$C_{1-5}$alkyl-, —$C_{1-5}$alkyl-CO—NR$^{14}$—$C_{1-5}$alkyl-, —$C_{1-6}$alkyl-CO—NH—, —$C_{1-6}$alkyl-NH—CO—, —CO—NH—$C_{1-6}$alkyl-, —NH—CO—$C_{1-6}$alkyl-, —CO—$C_{1-7}$alkyl-, —$C_{1-7}$alkyl-CO—, $C_{1-6}$alkyl-CO—$C_{1-6}$alkyl, —$C_{1-2}$alkyl-NH—CO—CH$_2$R$^{15}$—NH—;

X$^1$ represents a direct bond, O, —O—$C_{1-2}$alkyl-, CO, —CO—$C_{1-2}$alkyl-, NR$^{10}$, —NR$^{10}$—$C_{1-2}$alkyl-, NR$^{16}$—CO—, NR$^{16}$—CO—$C_{1-2}$alkyl, —O—N=CH— or $C_{1-2}$alkyl;

X$^2$ represents a direct bond, O, —O—$C_{1-2}$alkyl-, CO, —CO—$C_{1-2}$alkyl-, NR$^{11}$, NR$^{11}$—$C_{1-2}$alkyl-, NR$^{17}$—CO—, NR$^{17}$—CO—$C_{1-2}$alkyl, Het$^{20}$-$C_{1-2}$alkyl, —O—N=CH— or $C_{1-2}$alkyl;

R$^1$ represents hydrogen, cyano, halo, hydroxy, formyl, $C_{1-6}$alkoxy-, $C_{1-6}$alkyl-, $C_{1-6}$alkoxy- substituted with halo, $C_{1-4}$alkyl substituted with one or where possible two or more substituents selected from hydroxy or halo;

R$^2$ represents hydrogen, cyano, halo, hydroxy, hydroxycarbonyl-, Het$^{16}$-carbonyl-, $C_{1-4}$alkyloxycarbonyl-, $C_{1-4}$alkylcarbonyl-, aminocarbonyl-, mono- or di($C_{1-4}$alkyl)aminocarbonyl-, Het$^1$, formyl, $C_{1-4}$alkyl-, $C_{2-6}$alkynyl-, $C_{3-6}$cycloalkyl-, $C_{3-6}$cycloalkyloxy-, $C_{1-6}$alkoxy-, Ar$^5$, Ar$^1$-oxy-, dihydroxyborane, $C_{1-6}$alkoxy- substituted with halo, $C_{1-4}$alkyl substituted with one or where possible two or more substituents selected from halo, hydroxy or NR$^4$R$^5$, $C_{1-4}$alkylcarbonyl- wherein said $C_{1-4}$alkyl is optionally substituted with one or where possible two or more substituents selected from hydroxy or $C_{1-4}$alkyl-oxy-;

R$^3$ represents hydrogen, hydroxy, Ar$^3$-oxy, Ar$^4$—$C_{1-4}$alkyloxy-, $C_{1-4}$alkyloxy-, $C_{2-4}$alkenyloxy- optionally substituted with Het$^{12}$ or R$^3$ represents $C_{1-4}$alkyloxy substituted with one or where possible two or more substituents selected from $C_{1-4}$alkyloxy-, hydroxy, halo, Het$^2$-, —NR$^6$R$^7$, -carbonyl- NR$^8$R$^9$ or Het$^3$-carbonyl-;

R$^4$ and R$^5$ are each independently selected from hydrogen or $C_{1-4}$alkyl;

R$^6$ and R$^7$ are each independently selected from hydrogen, $C_{1-4}$alkyl, Het$^8$, aminosulfonyl-, mono- or di($C_{1-4}$alkyl)-aminosulfonyl, hydroxy-$C_{1-4}$alkyl-, $C_{1-4}$alkyl-oxy-$C_{1-4}$alkyl-, hydroxycarbonyl-$C_{1-4}$alkyl-, $C_{3-6}$cycloalkyl, Het$^9$-carbonyl-$C_{1-4}$alkyl-, Het$^{10}$-carbonyl-, polyhydroxy-$C_{1-4}$alkyl-, Het$^{11}$-$C_{1-4}$alkyl- or Ar$^2$—$C_{1-4}$alkyl-;

R$^8$ and R$^9$ are each independently selected from hydrogen, $C_{1-4}$alkyl, $C_{3-6}$cycloalkyl, Het$^4$, hydroxy-$C_{1-4}$alkyl-, $C_{1-4}$alkyloxyC$_{1-4}$alkyl- or polyhydroxy-$C_{1-4}$alkyl-;

R$^{10}$ represents hydrogen, $C_{1-4}$alkyl, Het$^5$, Het$^6$-$C_{1-4}$alkyl-, $C_{2-4}$alkenylcarbonyl-optionally substituted with Het$^7$-$C_{1-4}$alkylaminocarbonyl-, $C_{2-4}$alkenylsulfonyl-, $C_{1-4}$alkyloxyC$_{1-4}$alkyl- or phenyl optionally substituted with one or where possible two or more substituents selected from hydrogen, hydroxy, amino or $C_{1-4}$alkyloxy-;

R$^{11}$ represents hydrogen, $C_{1-4}$alkyl, $C_{1-4}$alkyl-oxy-carbonyl-, Het$^{17}$, Het$^{18}$-$C_{1-4}$alkyl-, $C_{2-4}$alkenylcarbonyl- optionally substituted with Het$^{19}$-$C_{1-4}$alkylaminocarbonyl-, $C_{2-4}$alkenylsulfonyl-, $C_{1-4}$alkyloxyC$_{1-4}$alkyl- or phenyl optionally substituted with one or where possible two or more substituents selected from hydrogen, hydroxy, amino or $C_{1-4}$alkyloxy-;

R$^{12}$ represents hydrogen, $C_{1-4}$alkyl, Het$^{13}$, Het$^{14}$-$C_{1-4}$alkyl- or phenyl optionally substituted with one or where possible two or more substituents selected from hydrogen, hydroxy, amino or $C_{1-4}$alkyloxy-;

R$^{13}$ and R$^{14}$ are each independently selected from hydrogen, $C_{1-4}$alkyl, Het$^{15}$-$C_{1-4}$alkyl- or $C_{1-4}$alkyloxyC$_{1-4}$alkyl-;

R$^{15}$ represents hydrogen or $C_{1-4}$alkyl optionally substituted with phenyl, indolyl, methylsulfide, hydroxy, thiol, hydroxyphenyl, aminocarbonyl, hydroxycarbonyl, amine, imidazoyl or guanidino;

R$^{16}$ and R$^{17}$ are each independently selected from hydrogen, $C_{1-4}$alkyl, Het$^{21}$-$C_{1-4}$alkyl or $C_{1-4}$alkyloxyC$_{1-4}$alkyl;

Het$^1$ represents a heterocycle selected from piperidinyl, morpholinyl, piperazinyl, furanyl, pyrazolyl, dioxolanyl, thiazolyl, oxazolyl, imidazolyl, isoxazolyl, oxadiazolyl, pyridinyl or pyrrolidinyl wherein said Het$^1$ is optionally substituted amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl- mono- or di($C_{1-4}$alkyl)amino- or amino-carbonyl-;

Het$^2$ represents a heterocycle selected from morpholinyl, piperazinyl, piperidinyl, pyrrolidinyl, thiomorpholinyl or dithianyl wherein said Het$^2$ is optionally substituted with one or where possible two or more substituents selected from hydroxy, halo, amino, $C_{1-4}$alkyl-, hydroxy-$C_{1-4}$alkyl-, $C_{1-4}$alkyl-oxy-$C_{1-4}$alkyl-, hydroxy-$C_{1-4}$alkyl-oxy-$C_{1-4}$alkyl-, mono- or di($C_{1-4}$alkyl)amino-, mono- or di($C_{1-4}$alkyl)amino-$C_{1-4}$alkyl-, aminoC$_{1-4}$alkyl-, mono- or di($C_{1-4}$alkyl)amino-sulfonyl-, aminosulfonyl-;

Het$^3$, Het$^4$ and Het$^8$ each independently represent a heterocycle selected from morpholinyl, piperazinyl, piperidinyl, furanyl, pyrazolyl, dioxolanyl, thiazolyl, oxazolyl, imidazolyl, isoxazolyl, oxadiazolyl, pyridinyl or pyrrolidinyl wherein said Het$^3$, Het$^4$ or Het$^8$ is optionally substituted with one or where possible two or more substituents selected from hydroxy-, amino-, $C_{1-4}$alkyl-, $C_{3-6}$cycloalkyl-$C_{1-4}$alkyl-, aminosulfonyl-, mono- or di($C_{1-4}$alkyl)aminosulfonyl or amino-$C_{1-4}$alkyl-;

Het$^5$ represent a heterocycle selected from pyrrolidinyl or piperidinyl wherein said heterocycle is optionally substituted with one or where possible two or more substituents selected from $C_{1-4}$alkyl, $C_{3-6}$cycloalkyl, hydroxy-$C_{1-4}$alkyl-, $C_{1-4}$alkyloxyC$_{1-4}$alkyl or polyhydroxy-$C_{1-4}$alkyl-;

Het$^6$ and Het$^7$ each independently represent a heterocycle selected from morpholinyl, pyrrolidinyl, piperazinyl or piperidinyl wherein said heterocycle is optionally substituted with one or where possible two or more substituents selected from $C_{1-4}$alkyl, $C_{3-6}$cycloalkyl, hydroxy-$C_{1-4}$alkyl-, $C_{1-4}$alkyloxyC$_{1-4}$alkyl or polyhydroxy-$C_{1-4}$alkyl-;

Het$^9$ and Het$^{10}$ each independently represent a heterocycle selected from furanyl, piperidinyl, morpholinyl, piperazinyl, pyrazolyl, dioxolanyl, thiazolyl, oxazolyl, imidazolyl, isoxazolyl, oxadiazolyl, pyridinyl or pyrrolidinyl wherein said Het$^9$ or Het$^{10}$ is optionally substituted $C_{1-4}$alkyl, $C_{3-6}$cycloalkyl-$C_{1-4}$alkyl- or amino-$C_{1-4}$alkyl-;

Het$^{11}$ represents a heterocycle selected from indolyl or

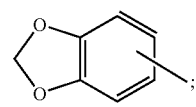

Het$^{12}$ represents a heterocycle selected from morpholinyl, piperazinyl, piperidinyl, pyrrolidinyl, thiomorpholinyl or dithianyl wherein said $Het^{12}$ is optionally substituted with one or where possible two or more substituents selected from hydroxy, halo, amino, $C_{1-4}$alkyl-, hydroxy-$C_{1-4}$alkyl-, $C_{1-4}$alkyl-oxy-$C_{1-4}$alkyl-, hydroxy-$C_{1-4}$alkyl-oxy-$C_{1-4}$alkyl-, mono- or di($C_{1-4}$alkyl)amino- or mono- or di($C_{1-4}$alkyl)amino-$C_{1-4}$alkyl-;

$Het^{13}$ represent a heterocycle selected from pyrrolidinyl or piperidinyl wherein said heterocycle is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{14}$ represent a heterocycle selected from morpholinyl, pyrrolidinyl, piperazinyl or piperidinyl wherein said heterocycle is optionally substituted with one or where possible two or more substituents selected from $C_{1-4}$alkyl, $C_{3-6}$cycloalkyl, hydroxy-$C_{1-4}$allkyl-, $C_{1-4}$alkyloxy$C_{1-4}$alkyl or polyhydroxy-$C_{1-4}$alkyl-;

$Het^{15}$ and $Het^{21}$ each independently represent a heterocycle selected from morpholinyl, pyrrolidinyl, piperazinyl or piperidinyl wherein said heterocycles are optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{16}$ represent a heterocycle selected from morpholinyl, pyrrolidinyl, piperazinyl, 1,3,2-dioxaborolane or piperidinyl wherein said heterocycle is optionally substituted with one or more substituents selected from $C_{1-4}$alkyl; and $Het^{17}$ represent a heterocycle selected from pyrrolidinyl or piperidinyl wherein said heterocycle is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{18}$ and $Het^{19}$ each independently represent a heterocycle selected from morpholinyl, pyrrolidinyl, piperazinyl or piperidinyl wherein said heterocycles are optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{20}$ represents a heterocycle selected from pyrrolidinyl, 2-pyrrolidinyl, piperidinyl, piperazinyl, morpholinyl, imidazolyl or pyrazolidinyl wherein said heterocycle is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-; in particular $Het^{20}$ represents a heterocycle selected from pyrrolidinyl, 2-pyrrolidinyl, piperidinyl, piperazinyl or pyrazolidinyl wherein said heterocycle is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-; and $Ar^1$, $Ar^2$, $Ar^3$, $Ar^4$ and $Ar^5$ each independently represent phenyl optionally substituted with cyano, $C_{1-4}$alkylsulfonyl-, $C_{1-4}$alkylsulfonylamino-, aminosulfonylamino-, hydroxy-$C_{1-4}$alkyl, aminosulfonyl-, hydroxy-, $C_{1-4}$alkyloxy- or $C_{1-4}$alkyl.

As used in the foregoing definitions and hereinafter,
halo is generic to fluoro, chloro, bromo and iodo;
$C_{1-2}$alkyl defines methyl or ethyl;
$C_{1-3}$alkyl defines straight and branched chain saturated hydrocarbon radicals having from 1 to 3 carbon atoms such as, for example, methyl, ethyl, propyl and the like;
$C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl, 2,2-dimethylethyl and the like;
$C_{1-5}$alkyl defines straight and branched chain saturated hydrocarbon radicals having from 1 to 5 carbon atoms such as, for example, methyl, ethyl, propyl, butyl, pentyl, 1-methylbutyl, 2,2-dimethylpropyl, 2,2-dimethylethyl and the like;
$C_{1-6}$alkyl is meant to include $C_{1-5}$alkyl and the higher homologues thereof having 6 carbon atoms such as, for example hexyl, 1,2-dimethylbutyl, 2-methylpentyl and the like;
$C_{1-7}$alkyl is meant to include $C_{1-6}$alkyl and the higher homologues thereof having 7 carbon atoms such as, for example 1,2,3-dimethylbutyl, 1,2-methylpentyl and the like;
$C_{3-9}$alkyl defines straight and branched chain saturated hydrocarbon radicals having from 3 to 9 carbon atoms such as propyl, butyl, pentyl, hexyl, heptyl, octyl, nonyl and the like;
$C_{2-4}$alkenyl defines straight and branched chain hydrocarbon radicals containing one double bond and having from 2 to 4 carbon atoms such as, for example vinyl, 2-propenyl, 3-butenyl, 2-butenyl and the like;
$C_{3-9}$alkenyl defines straight and branched chain hydrocarbon radicals containing one double bond and having from 3 to 9 carbon atoms such as, for example 2-propenyl, 3-butenyl, 2-butenyl, 2-pentenyl, 3-pentenyl, 3-methyl-2-butenyl, 3-hexenyl and the like;
$C_{2-6}$alkynyl defines straight and branched chain hydrocarbon radicals containing one triple bond and having from 2 to 6 carbon atoms such as, for example, 2-propynyl, 3-butynyl, 2-butynyl, 2-pentynyl, 3-pentynyl, 3-methyl-2-butynyl, 3-hexynyl and the like;
$C_{3-6}$cycloalkyl is generic to cyclopropyl, cyclobutyl, cyclopentyl and cyclohexyl;
$C_{1-4}$alkyloxy defines straight or branched saturated hydrocarbon radicals such as methoxy, ethoxy, propyloxy, butyloxy, 1-methylethyloxy, 2-methylpropyloxy and the like;
$C_{1-6}$alkyloxy is meant to include $C_{1-4}$alkyloxy and the higher homologues such as methoxy, ethoxy, propyloxy, butyloxy, 1-methylethyloxy, 2-methylpropyloxy and the like;
polyhydroxy-$C_{1-4}$alkyl is generic to a $C_{1-4}$alkyl as defined hereinbefore, having two, three or were possible more hydroxy substituents, such as for example trifluoromethyl.

As used in the foregoing definitions and hereinafter, the term formyl refers to a radical of formula —CH(=O).

The heterocycles as mentioned in the above definitions and hereinafter, are meant to include all possible isomeric forms thereof, for instance pyrrolyl also includes 2H-pyrrolyl; triazolyl includes 1,2,4-triazolyl and 1,3,4-triazolyl; oxadiazolyl includes 1,2,3-oxadiazolyl, 1,2,4-oxadiazolyl, 1,2,5-oxadiazolyl and 1,3,4-oxadiazolyl; thiadiazolyl includes 1,2,3-thiadiazolyl, 1,2,4-thiadiazolyl, 1,2,5-thiadiazolyl and 1,3,4-thiadiazolyl; pyranyl includes 2H-pyranyl and 4H-pyranyl.

Further, the heterocycles as mentioned in the above definitions and hereinafter may be attached to the remainder of the molecule of formula (I) through any ring carbon or heteroatom as appropriate. Thus, for example, when the heterocycle is imidazolyl, it may be a 1-imidazolyl, 2-imidazolyl, 3-imidazolyl, 4-imidazolyl and 5-imidazolyl; when it is thiazolyl, it may be 2-thiazolyl, 4-thiazolyl and 5-thiazolyl; when it is triazolyl, it may be 1,2,4-triazol-1-yl, 1,2,4-triazol-3-yl, 1,2,4-triazol-5-yl, 1,3,4-triazol-1-yl and 1,3,4-triazol-2-yl;

when it is benzothiazolyl, it may be 2-benzothiazolyl, 4-benzothiazolyl, 5-benzothiazolyl, 6-benzothiazolyl and 7-benzothiazolyl.

The pharmaceutically acceptable addition salts as mentioned hereinabove are meant to comprise the therapeutically active non-toxic acid addition salt forms which the compounds of formula (I) are able to form. The latter can conveniently be obtained by treating the base form with such appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butane-dioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The pharmaceutically acceptable addition salts as mentioned hereinabove are meant to comprise the therapeutically active non-toxic base addition salt forms which the compounds of formula (I) are able to form. Examples of such base addition salt forms are, for example, the sodium, potassium, calcium salts, and also the salts with pharmaceutically acceptable amines such as, for example, ammonia, alkylamines, benzathine, N-methyl-D-glucamine, hydrabamine, amino acids, e.g. arginine, lysine.

Conversely said salt forms can be converted by treatment with an appropriate base or acid into the free acid or base form.

The term addition salt as used hereinabove also comprises the solvates which the compounds of formula (I) as well as the salts thereof, are able to form. Such solvates are for example hydrates, alcoholates and the like.

The term stereochemically isomeric forms as used hereinbefore defines the possible different isomeric as well as conformational forms which the compounds of formula (I) may possess. Unless otherwise mentioned or indicated, the chemical designation of compounds denotes the mixture of all possible stereochemically and conformationally isomeric forms, said mixtures containing all diastereomers, enantiomers and/or conformers of the basic molecular structure. All stereochemically isomeric forms of the compounds of formula (I) both in pure form or in admixture with each other are intended to be embraced within the scope of the present invention.

Some of the compounds of formula (I) may also exist in their tautomeric forms. Such forms although not explicitly indicated in the above formula are intended to be included within the scope of the present invention.

The N-oxide forms of the compounds of formula (I) are meant to comprise those compounds of formula (I) wherein one or several nitrogen atoms are oxidized to the so-called N-oxide.

A preferred group of compounds consists of those compounds of formula (I) wherein one or more of the following restrictions apply:

Z represents NH;

Y represents —$C_{3-9}$alkyl-, —$C_{2-9}$alkenyl-, —$C_{1-5}$alkyl-oxy-$C_{1-5}$alkyl-, —$C_{1-5}$alkyl-NR$^{12}$—$C_{1-5}$alkyl-, —$C_{1-6}$alkyl-NH—CO—, —CO—$C_{1-7}$alkyl-, —$C_{1-7}$alkyl-CO— or $C_{1-6}$alkyl-CO—$C_{1-6}$alkyl;

$X^1$ represents O, —O—$C_{1-2}$alkyl-, —O—N=CH—, NR$^{10}$ or —NR$^{10}$—$C_{1-2}$alkyl-; in a particular embodiment $X^1$ represents —O— or —O—CH$_2$—;

$X^2$ represents a direct bond, O, —O—$C_{1-2}$alkyl-, —O—N=CH—, $C_{1-2}$alkyl, NR$^{11}$ or NR$^{11}$—$C_{1-2}$alkyl-; in a particular embodiment $X^2$ represents a direct bond, —O—N=CH—, —NR$^{11}$—$C_{1-2}$alkyl-, —NR$^{11}$—CH$_2$—, —$C_{1-2}$alkyl-, —O—$C_{1-2}$alkyl, O— or —O—CH$_2$—;

$R^1$ represents hydrogen, cyano, halo or hydroxy, preferably halo;

$R^2$ represents hydrogen, cyano, halo, hydroxy, hydroxycarbonyl-, $C_{1-4}$alkyloxycarbonyl-, Het$^{16}$-carbonyl-, $C_{2-6}$alkynyl-, Ar$^5$ or Het$^1$; In a further embodiment $R^2$ represents hydrogen, cyano, halo, hydroxy, $C_{2-6}$alkynyl- or Het$^1$;

$R^3$ represents hydrogen, hydroxy, $C_{1-4}$alkyloxy-, Ar$^4$—$C_{1-4}$alkyloxy or $R^3$ represents $C_{1-4}$alkyloxy substituted with one or where possible two or more substituents selected from $C_{1-4}$alkyloxy- or Het$^2$-;

$R^{10}$ represents hydrogen, $C_{1-4}$alkyl- or $C_{1-4}$alkyl-oxy-carbonyl-;

$R^{11}$ represents hydrogen, $C_{1-4}$alkyl- or $C_{1-4}$alkyl-oxy-carbonyl-;

$R^{12}$ represents Het$^{14}$-$C_{1-4}$alkyl, in particular morpholinyl-$C_{1-4}$alkyl;

Het$^1$ represents thiazolyl optionally substituted amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl- mono- or di($C_{1-4}$alkyl)amino- or amino-carbonyl-;

Het$^2$ represents a heterocycle selected from morpholinyl, piperazinyl, piperidinyl or pyrrolidinyl wherein said Het$^2$ is optionally substituted with one or where possible two or more substituents selected from hydroxy, amino or $C_{1-4}$alkyl-; In a further embodiment Het$^2$ represents a heterocycle selected from morpholinyl or piperidinyl optionally substituted with $C_{1-4}$alkyl-, preferably methyl;

Het$^{14}$ represents a heterocycle selected from morpholinyl, piperazinyl, piperidinyl or pyrrolidinyl wherein said Het$^{14}$ is optionally substituted with one or where possible two or more substituents selected from hydroxy, amino or $C_{1-4}$alkyl-;

Het$^{16}$ represents a heterocycle selected from piperidinyl, morpholinyl or pyrrolidinyl;

Ar$^4$ represents phenyl optionally substituted with cyano, hydroxy-, $C_{1-4}$alkyloxy or $C_{1-4}$alkyl;

Ar$^5$ represents phenyl optionally substituted with cyano, hydroxy, $C_{1-4}$alkyloxy or $C_{1-4}$alkyl.

A further group of compounds consists of those compounds of formula (I) wherein one or more of the following restrictions apply:

Z represents NH;

Y represents —$C_{3-9}$alkyl-, —$C_{1-5}$alkyl-NR$^{12}$—$C_{1-5}$alkyl-, —$C_{1-6}$alkyl-NH—CO— or —CO—NH—$C_{1-6}$alkyl-;

$X^1$ represents —O—;

$X^2$ represents a direct bond, —NR$^{11}$—$C_{1-2}$alkyl-, —NR$^{11}$—CH$_2$—, —$C_{1-2}$alkyl-, —O—$C_{1-2}$alkyl, —O— or —O—CH$_2$—;

$R^1$ represents hydrogen or halo;

$R^2$ represents hydrogen, cyano, halo, hydroxycarbonyl-, $C_{1-4}$alkyloxycarbonyl-, Het$^{16}$-carbonyl- or Ar$^5$;

$R^3$ represents hydrogen, hydroxy, $C_{1-4}$alkyloxy-, Ar$^4$—$C_{1-4}$alkyloxy or $R^3$ represents $C_{1-4}$alkyloxy substituted with one or where possible two or more substituents selected from $C_{1-4}$alkyloxy- or Het$^2$-;

$R^{10}$ represents hydrogen;

$R^{11}$ represents hydrogen, $C_{1-4}$alkyl- or $C_{1-4}$alkyl-oxy-carbonyl-;

$R^{12}$ represents Het$^{14}$-$C_{1-4}$alkyl, in particular morpholinyl-$C_{1-4}$alkyl;

Het$^2$ represents a heterocycle selected from morpholinyl, piperazinyl, piperidinyl or pyrrolidinyl wherein said Het$^2$ is optionally substituted with one or where possible two or more substituents selected from hydroxy, amino or $C_{1-4}$alkyl-; In a further embodiment Het$^2$ represents a heterocycle selected from morpholinyl or piperidinyl optionally substituted with $C_{1-4}$alkyl-, preferably methyl;

Het$^{14}$ represents morpholinyl;

Het$^{16}$ represents a heterocycle selected from morpholinyl or pyrrolidinyl;

Ar$^4$ represents phenyl;

Ar$^5$ represents phenyl optionally substituted with cyano.

Another group of compounds consists of those compounds of formula (I) wherein one or more of the following restrictions apply:

Z represents NH;

Y represents —$C_{3-9}$alkyl-, —$C_{2-9}$alkenyl-, —$C_{1-5}$alkyl-oxy-$C_{1-5}$alkyl-, —$C_{1-5}$alkyl-NR$^{12}$—$C_{1-5}$alkyl-, —$C_{1-5}$alkyl-NR$^{13}$—CO—$C_{1-5}$alkyl-, —$C_{1-6}$alkyl-NH—CO—, —CO—$C_{1-7}$alkyl-, —$C_{1-7}$alkyl-CO— or $C_{1-6}$alkyl-CO—$C_{1-6}$alkyl;

X$^1$ represents O, —O—$C_{1-2}$alkyl-, —O—N=CH—, NR$^{16}$—CO, —NR$^{16}$—CO—$C_{1-2}$alkyl-, NR$^{10}$ or —NR$^{10}$—$C_{1-2}$alkyl-; in a particular embodiment X$^1$ represents —O—, —O—CH$_2$—, NR$^{10}$ or —NR$^{10}$—$C_{1-2}$alkyl-;

X$^2$ represents a direct bond, O, —O—$C_{1-2}$alkyl-, —O—N=CH—, Het$^{20}$-$C_{1-2}$alkyl, $C_{1-2}$alkyl, NR$^{17}$—CO, —NR$^{17}$—CO—$C_{1-2}$alkyl-, NR$^{11}$ or NR$^{11}$—$C_{1-2}$alkyl-; in a particular embodiment X$^2$ represents a direct bond, —O—N=CH—, —NR$^{11}$—$C_{1-2}$alkyl-, —NR$^{11}$—CH$_2$—, Het$^{20}$-$C_{1-2}$alkyl, NR$^{17}$—CO, —NR$^{17}$—CO—$C_{1-2}$alkyl- —$C_{1-2}$alkyl-, —O—$C_{1-2}$alkyl, —O— or —O—CH$_2$—;

R$^1$ represents hydrogen, cyano, halo or hydroxy, preferably halo;

R$^2$ represents hydrogen, cyano, halo, hydroxy, hydroxycarbonyl-, $C_{1-4}$alkyloxycarbonyl-, Het$^{16}$-carbonyl-, $C_{2-6}$alkynyl-, Ar$^5$ or Het$^1$; In a further embodiment R$^2$ represents hydrogen, cyano, halo, hydroxy, $C_{2-6}$alkynyl- or Het$^1$;

R$^3$ represents hydrogen, hydroxy, $C_{1-4}$alkyloxy-, Ar$^4$—$C_{1-4}$alkyloxy or R$^3$ represents $C_{1-4}$alkyloxy substituted with one or where possible two or more substituents selected from $C_{1-4}$alkyloxy- or Het$^2$-;

R$^{10}$ represents hydrogen, $C_{1-4}$alkyl- or $C_{1-4}$alkyl-oxy-carbonyl-;

R$^{11}$ represents hydrogen, $C_{1-4}$alkyl- or $C_{1-4}$alkyl-oxy-carbonyl-;

R$^{12}$ represents Het$^{14}$-$C_{1-4}$alkyl, in particular morpholinyl-$C_{1-4}$alkyl;

R$^{16}$ represents hydrogen, $C_{1-4}$alkyl-, Het$^{21}$-$C_{1-4}$alkyl or $C_{1-4}$alkyl-oxy-$C_{1-4}$alkyl; in particular R$^{16}$ represents hydrogen or $C_{1-4}$alkyl;

R$^{17}$ represents hydrogen, $C_{1-4}$alkyl-, Het$^{21}$-$C_{1-4}$alkyl or $C_{1-4}$alkyl-oxy-$C_{1-4}$alkyl; in particular R$^{16}$ represents hydrogen or $C_{1-4}$alkyl;

Het$^1$ represents thiazolyl optionally substituted amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl- mono- or di($C_{1-4}$alkyl)amino- or amino-carbonyl-;

Het$^2$ represents a heterocycle selected from morpholinyl, piperazinyl, piperidinyl or pyrrolidinyl wherein said Het$^2$ is optionally substituted with one or where possible two or more substituents selected from hydroxy, amino or $C_{1-4}$alkyl-; In a further embodiment Het$^2$ represents a heterocycle selected from morpholinyl or piperidinyl optionally substituted with $C_{1-4}$alkyl-, preferably methyl;

Het$^{14}$ represents a heterocycle selected from morpholinyl, piperazinyl, piperidinyl or pyrrolidinyl wherein said Het$^{14}$ is optionally substituted with one or where possible two or more substituents selected from hydroxy, amino or $C_{1-4}$alkyl-;

Het$^{16}$ represents a heterocycle selected from piperidinyl, morpholinyl or pyrrolidinyl;

Het$^{20}$ represents a heterocycle selected from pyrrolidinyl, 2-pyrrolidinyl or piperidinyl;

Het$^{21}$ represents a heterocycle selected from morpholinyl, piperazinyl, piperidinyl or pyrrolidinyl wherein said Het$^{21}$ is optionally substituted with one or where possible two or more substituents selected from hydroxy, amino or $C_{1-4}$alkyl-;

Ar$^4$ represents phenyl optionally substituted with cyano, hydroxy-, $C_{1-4}$alkyloxy or $C_{1-4}$alkyl;

Ar$^5$ represents phenyl optionally substituted with cyano, hydroxy, $C_{1-4}$alkyloxy or $C_{1-4}$alkyl.

A further group of compounds consists of those compounds of formula (I) wherein one or more of the following restrictions apply:

Z represents NH;

Y represents —$C_{3-9}$alkyl-, —$C_{1-5}$alkyl-NR$^{12}$—$C_{1-5}$alkyl-, —$C_{1-5}$alkyl-NR$^{13}$—CO—$C_{1-5}$alkyl-, —$C_{1-5}$alkyl-CO—NR$^{14}$—$C_{1-5}$alkyl-, —$C_{1-6}$alkyl-NH—CO— or —CO—NH—$C_{1-6}$alkyl-; in particular Y represents —$C_{3-9}$alkyl-, —$C_{1-5}$alkyl-NR$^{12}$—$C_{1-5}$alkyl-, —$C_{1-5}$alkyl-NR$^{13}$—CO—$C_{1-5}$alkyl-, —$C_{1-6}$alkyl-NH—CO— or —CO—NH—$C_{1-6}$alkyl-;

X$^1$ represents a direct bond, NR$^{10}$, —NR$^{10}$—$C_{1-2}$alkyl-, —NR$^{10}$—CH$_2$—, —$C_{1-2}$alkyl-, —O—$C_{1-2}$alkyl, —O— or —O—CH$_2$—;

X$^2$ represents a —O—, NR$^{11}$, NR$^{17}$—CO, NR$^{17}$—CO—$C_{1-2}$alkyl or Het$^{20}$-$C_{1-2}$alkyl;

R$^1$ represents hydrogen or halo;

R$^2$ represents hydrogen, cyano, halo, hydroxycarbonyl-, $C_{1-4}$alkyloxycarbonyl-, Het$^{16}$-carbonyl- or Ar$^5$;

R$^3$ represents hydrogen, hydroxy, $C_{1-4}$alkyloxy-, Ar$^4$—$C_{1-4}$alkyloxy or R$^3$ represents $C_{1-4}$alkyloxy substituted with one or where possible two or more substituents selected from $C_{1-4}$alkyloxy- or Het$^2$-;

R$^{10}$ represents hydrogen;

R$^{11}$ represents hydrogen, $C_{1-4}$alkyl- or $C_{1-4}$alkyl-oxy-carbonyl-;

R$^{12}$ represents Het$^{14}$-$C_{1-4}$alkyl, in particular morpholinyl-$C_{1-4}$alkyl;

R$^{13}$ represents hydrogen;

R$^{17}$ represents hydrogen;

Het$^2$ represents a heterocycle selected from morpholinyl, piperazinyl, piperidinyl or pyrrolidinyl wherein said Het$^2$ is optionally substituted with one or where possible two or more substituents selected from hydroxy, amino or $C_{1-4}$alkyl-; In a further embodiment Het$^2$ represents a heterocycle selected from morpholinyl or piperidinyl optionally substituted with $C_{1-4}$alkyl-, preferably methyl;

Het$^{14}$ represents morpholinyl;

Het$^{16}$ represents a heterocycle selected from morpholinyl or pyrrolidinyl;

Het$^{20}$ represents pyrrolidinyl or piperidinyl;

Ar$^4$ represents phenyl;

Ar$^5$ represents phenyl optionally substituted with cyano.

Other special group of compounds are:
those compounds of formula (I) wherein —X$^1$— represents —O—;
those compounds of formula (I) wherein —X$^1$— represents —NR$^{10}$—, in particular —NH—;
those compounds of formula (I) wherein —X$^2$— represents —NR$^{17}$—CO—$C_{1-2}$alkyl-, in particular —NH—CO—$C_{1-2}$alkyl-;

those compounds of formula (I) wherein —X²— represents represents —NR¹¹—C₁₋₂alkyl, in particular —NH—C₁₋₂alkyl-;

those compounds of formula (I) wherein —Y— represents —C₁₋₅alkyl-NR¹³—CO—C₁₋₅alkyl- or —C₁₋₅alkyl-CO—NR¹⁴—C₁₋₅alkyl-, in particular —C₁₋₅alkyl-NH—CO—C₁₋₅alkyl-;

those compounds of formula (I) wherein R¹ is fluoro, chloro or bromo;

those compounds of formula (I) wherein R² is fluoro, chloro or bromo;

those compounds of formula (I) wherein R¹ and R² represent halo, in particular those compounds of formula (I) wherein R¹ represents fluoro and R² represents chloro;

those compounds of formula (I) wherein R² is Het¹, in particular thiazolyl optionally substituted with methyl;

those compounds of formula (I) wherein R² is C₂₋₆alkynyl-, in particular ethylyn;

those compounds of formula (I) wherein R² is Ar⁵, in particular phenyl optionally substituted with cyano;

those compounds of formula (I) wherein R³ represents methoxy and wherein said methoxy is at position 7 of the structure of formula (I).

those compounds of formula (I) wherein R³ represents C₁₋₄alkyloxy substituted with one substituent selected from C₁₋₄alkyloxy- or Het²-, in particular propyloxy substituted with morpholinyl;

those compounds of formula (I) wherein R¹¹ is hydrogen or C₁₋₄alkyl-, in particular methyl or wherein R¹¹ is C₁₋₄alkyl-oxy-carbonyl-, in particular t-butyl-oxy-carbonyl- those compounds of formula (I) wherein Het² represent morpholinyl optionally substituted with C₁₋₄alkyl, preferably morpholinyl attached through the nitrogen atom to the remainder of the compounds of formula (I);

those compounds of formula (I) with Het³ represent morpholinyl optionally substituted with C₁₋₄alkyl, preferably morpholinyl attached through the nitrogen atom to the remainder of the compounds of formula (I);

those compounds of formula (I) wherein Het¹² represent morpholinyl optionally substituted with C₁₋₄alkyl, preferably morpholinyl attached through the nitrogen atom to the remainder of the compounds of formula (I).

In a further embodiment of the present invention the R¹ substituent is at position 4', the R² substituent is at position 5' and the R³ substituent at position 7 of the structure of formula (I).

The compounds of this invention can be prepared by any of several standard synthetic processes commonly used by those skilled in the art of organic chemistry and described for instance in the following references; "Heterocyclic Compounds"—Vol. 24 (part4) p 261-304 Fused pyrimidines, Wiley—Interscience; Chem. Pharm. Bull., Vol 41(2) 362-368 (1993); J. Chem. Soc., Perkin Trans. 1, 2001, 130-137.

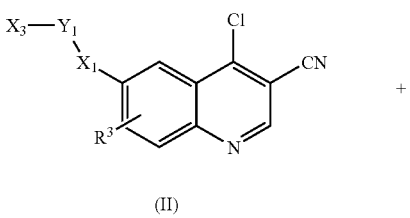

(II)

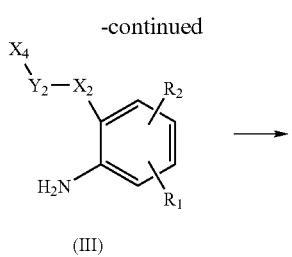

(III)

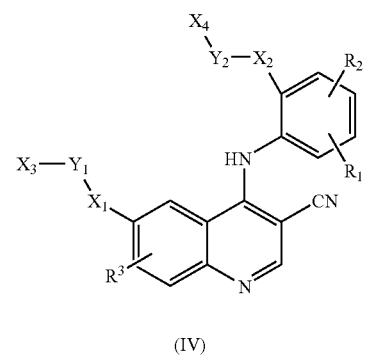

(IV)

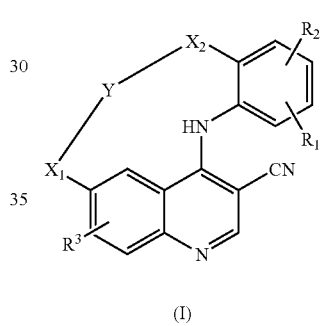

(I)

Y₁ and Y₂ represent a C₁₋₅alkyl or CO—C₁₋₅alkyl

X₃ and X₄ represent optionally protected functional groups, such as for example a primair, secundair or tertiair amine, hydroxy or halo (Cl, Br or I), which upon reaction produce together with the Y₁ respectively Y₂ substituent to which they are attached, the divalent Y radical as defined for formula (I)

As further exemplified in the experimental part of the description, the compounds of formula (I) wherein X¹ represents —O— were generally prepared starting from 6-acetoxy-4-chloro-3-cyanoquinolines of formula (II), which can be prepared from the known 5-acetoxy-4-alkoxy-2-nitrobenzoic acid (Scheme 2).

Coupling of this quinoline of formula (II) with suitable substituted anilines (III), which in their turn can be prepared according to reaction schemes 3-7, furnish the intermediate compounds (IV).

Deprotection of the intermediates of formula (IV) as described in *Protective Groups in Organic Synthesis* by T. W. Greene and P. G. M. Wuts, 3ʳᵈ edition, 1998 followed by ring closure under Mitsunobu conditions give the target compounds (I) (Scheme 1).

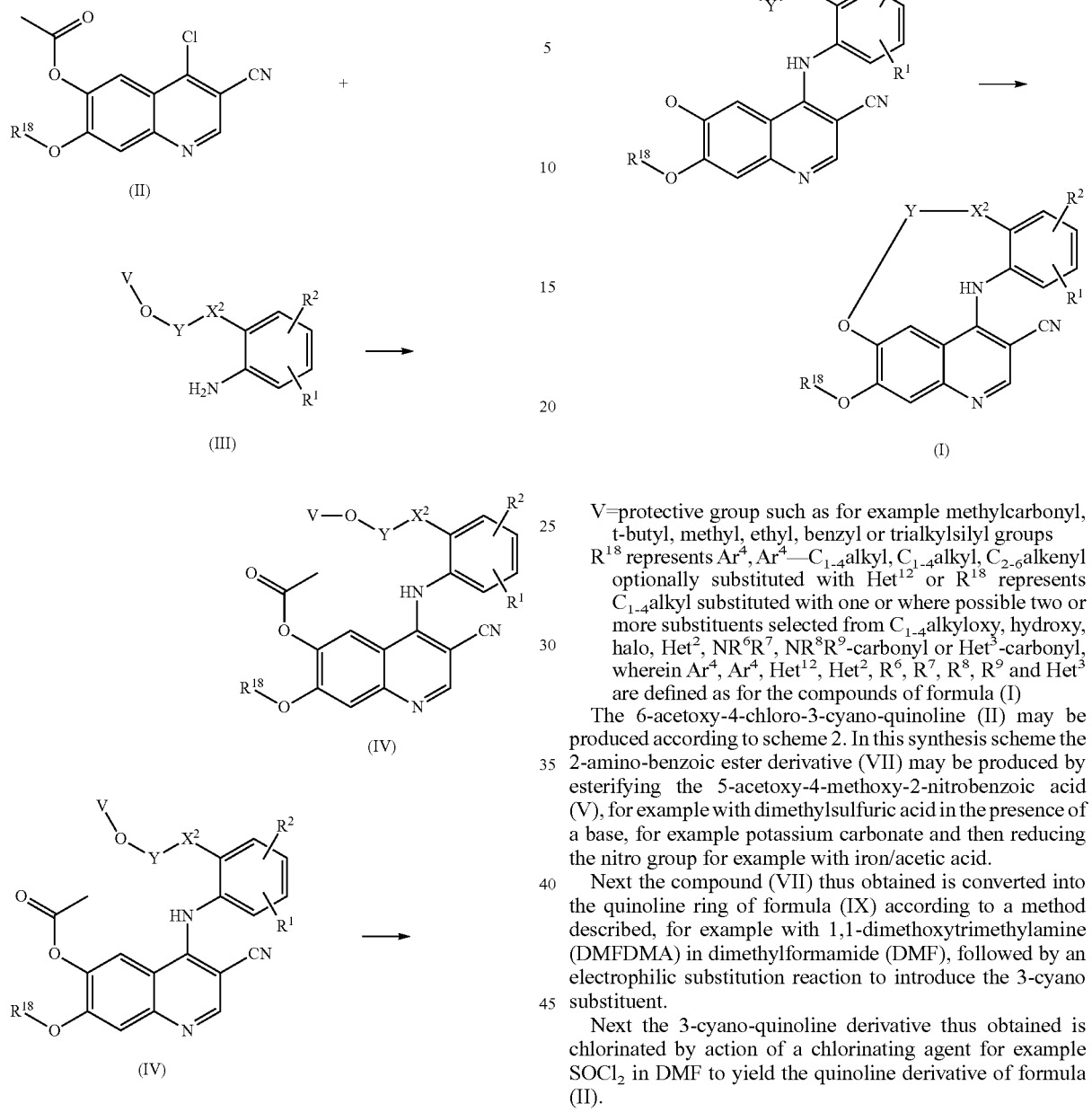

V=protective group such as for example methylcarbonyl, t-butyl, methyl, ethyl, benzyl or trialkylsilyl groups $R^{18}$ represents $Ar^4$, $Ar^4$—$C_{1-4}$alkyl, $C_{1-4}$alkyl, $C_{2-6}$alkenyl optionally substituted with $Het^{12}$ or $R^{18}$ represents $C_{1-4}$alkyl substituted with one or where possible two or more substituents selected from $C_{1-4}$alkyloxy, hydroxy, halo, $Het^2$, $NR^6R^7$, $NR^8R^9$-carbonyl or $Het^3$-carbonyl, wherein $Ar^4$, $Ar^4$, $Het^{12}$, $Het^2$, $R^6$, $R^7$, $R^8$, $R^9$ and $Het^3$ are defined as for the compounds of formula (I)

The 6-acetoxy-4-chloro-3-cyano-quinoline (II) may be produced according to scheme 2. In this synthesis scheme the 2-amino-benzoic ester derivative (VII) may be produced by esterifying the 5-acetoxy-4-methoxy-2-nitrobenzoic acid (V), for example with dimethylsulfuric acid in the presence of a base, for example potassium carbonate and then reducing the nitro group for example with iron/acetic acid.

Next the compound (VII) thus obtained is converted into the quinoline ring of formula (IX) according to a method described, for example with 1,1-dimethoxytrimethylamine (DMFDMA) in dimethylformamide (DMF), followed by an electrophilic substitution reaction to introduce the 3-cyano substituent.

Next the 3-cyano-quinoline derivative thus obtained is chlorinated by action of a chlorinating agent for example $SOCl_2$ in DMF to yield the quinoline derivative of formula (II).

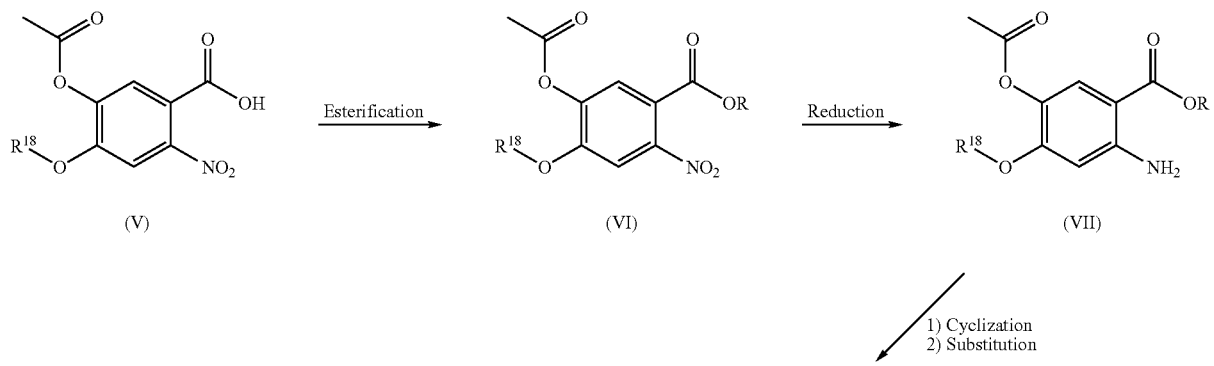

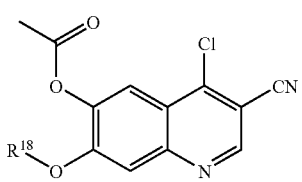  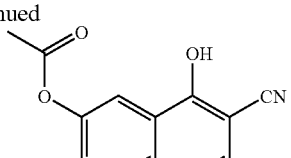

$R^{18}$ represents $Ar^3$, $Ar^4$—$C_{1-4}$alkyl, $C_{1-4}$alkyl, $C_{2-6}$alkenyl optionally substituted with $Het^{12}$ or $R^{18}$ represents $C_{1-4}$alkyl substituted with one or where possible two or more substituents selected from $C_{1-4}$alkyloxy, hydroxy, halo, $Het^2$, $NR^6R^7$, $NR^8R^9$-carbonyl or $Het^3$-carbonyl, wherein $Ar^3$, $Ar^4$, $Het^{12}$, $Het^2$, $R^6$, $R^7$, $R^8$, $R^9$ and $Het^3$ are defined as for the compounds of formula (I)

For those compounds where $X^2$ represents —O—, the suitable substituted anilines of formula (III$^a$) are generally prepared from the commercially available nitro-phenols (X) and the α,ω-protected halogenated alcohols (XI) under alkaline conditions in a reaction inert solvent, for example, using dimethylacetamide (DMA) in the presence of $K_2CO_3$. The resulting nitro-phenyl derivative (XII) is subsequently reduced according to standard conditions, for example, using iron/acetic acid, to yield the substituted anilines of formula (III$^a$) (Scheme 3).

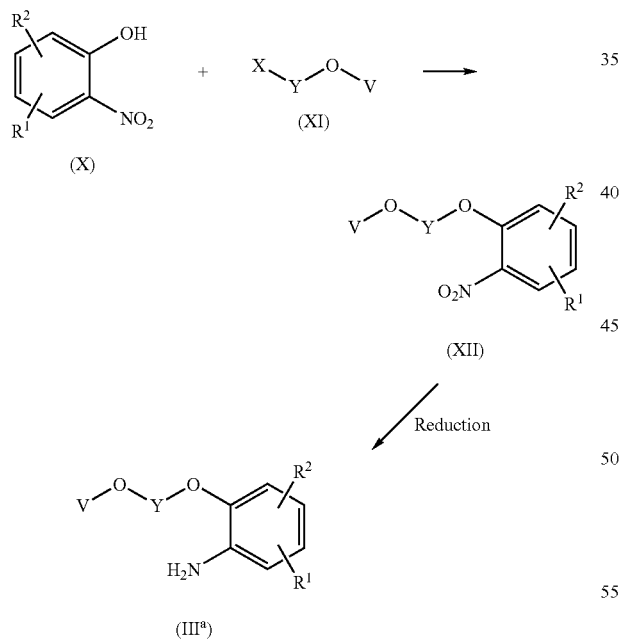

X represents a halogen such as for example, Cl, Br, I and F
V represents a protective group such as for example methylcarbonyl For those compounds where $X^2$ represents —$NR^{11}$— or —$NR^{11}$—$C_{1-2}$alkyl-, the suitable substituted anilines of formula (III$^b$) are generally prepared from the commercially available 2-nitro-benzaldehydes (XIII) and the amine substituted alcohols (XIV) by reductive amination under standard conditions, for example using $NaBH_4$ and titanium(iv)isopropoxide as reducing agents in ethanol as solvent, yielding in a first step the nitro-benzylamines of formula (XV).

Next the primary free alcohol is protected using art known procedures, for example, using an esterification reaction with acetic anhydride in the presence of pyridine.

The thus obtained intermediate of formula (XVI) is subsequently reduced according to standard conditions, for example, using iron/acetic acid to yield the substituted anilines of formula (III$^b$) (Scheme 4).

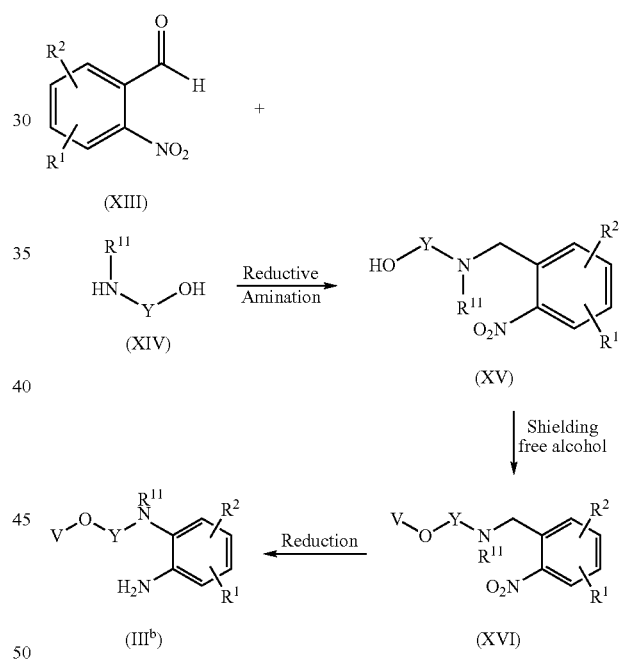

V represents a protective group such as for example methylcarbonyl

For those compounds where $X^2$ represents —O—N=CH—, the suitable substituted anilines of formula (III$^c$) are generally prepared according to reaction scheme 5.

In a first step the known 2-nitro-benzaldehydes (XIII) are converted into the corresponding oxime (XVII) using, for example, the art known condensation reaction with hydroxylamine Next said oxime of formula XVII is allowed to react with an halogenated alkylacetate under alkaline conditions, for example using $K_2CO_3$ in DMSO, followed by reducing the nitro group, for example, with iron/acetic acid, to provide the suitable substituted aniline of formula (III$^c$).

Scheme 5

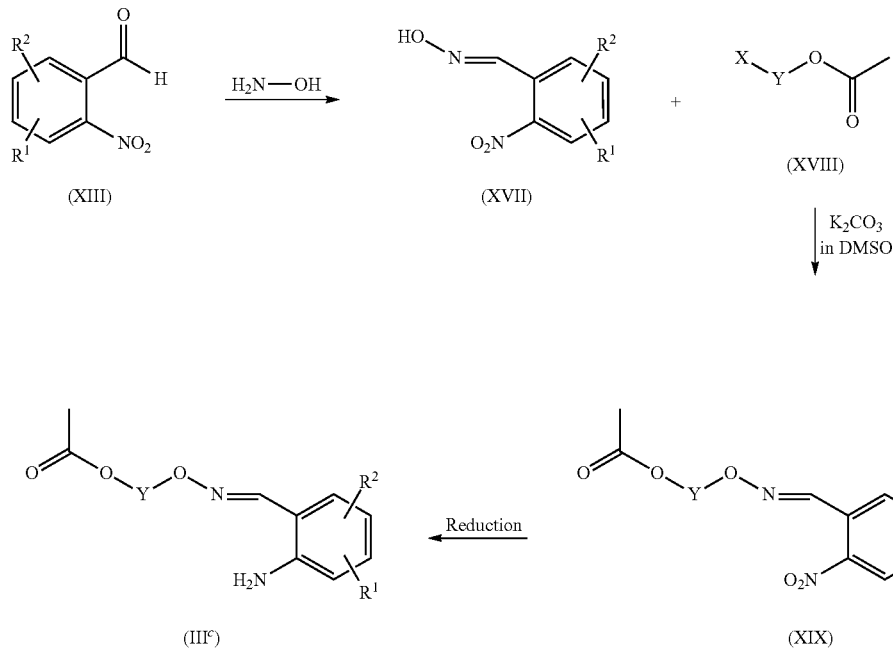

X represents a halogen such as for example Cl, Br, I or F

For those compounds where $X^2$ represents a direct bond and Y represents $C_{1-6}$alkyl-NH—CO—, the suitable substituted anilines of formula (III$^d$) are generally prepared according to reaction scheme 6.

In a first step the known 2-nitro-benzoic acids (XX) are amidated to the intermediates of formula (XXII) under art known conditions, for example, using a hydroxylated amine of formula (XXI) that is added dropwise to a mixture of (XX) in $CH_2Cl_2$ in the presence of 1,1' carbonylbis-1H-imidazole.

Next the primary free alcohol is protected using art known procedures, for example, using an esterification reaction with acetic anhydride in the presence of pyridine.

The thus obtained intermediate of formula (XXIII) is subsequently reduced according to standard conditions, for example, using iron/acetic acid to yield the substituted anilines of formula (III$^d$).

Scheme 6

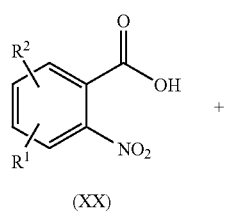

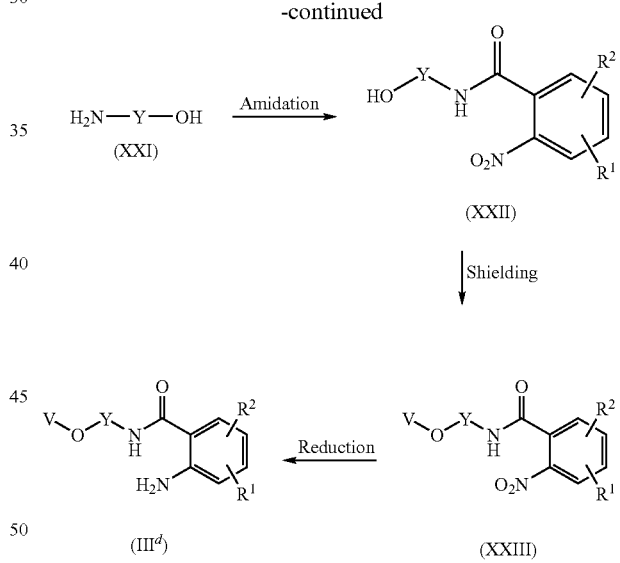

V represents a protective group such as for example methylcarbonyl

For those compounds where $X^2$ represents a direct bond the suitable substituted anilines of formula (III$^e$) are generally prepared according to reaction scheme 7.

In a first step the known 2-nitro-benzaldehydes (XIII) are alkenated to the intermediates of formula (XXV) under art known conditions, for example, using the Wittig Reaction with the appropriate phosphonium salt of formula (XXIV).

Following esterification of the free carboxylic acid under standard conditions for example, using ethanol under acidic conditions, the intermediate of formula (XXVI) are reduced to yield the desired substituted anilines of formula (III$^e$).

Scheme 7

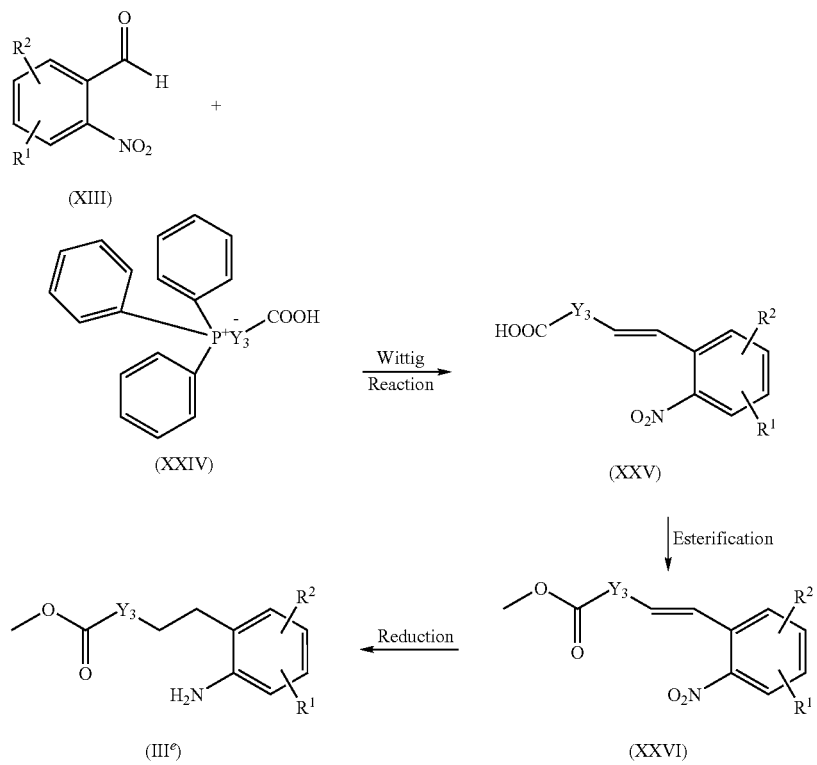

$Y_3$ represents a $C_{1-7}$alkyl

Alternatively, those compounds of formula (I'$^b$) wherein Y represents —$C_{1-5}$alkyl-NR$^{12}$—$C_{1-5}$alkyl-, —$C_{1-5}$alkyl-NR$^{13}$—CO—$C_{1-5}$alkyl-, —$C_{1-2}$alkyl-NH—CO—CH$_2$R$^{15}$—NH— or —$C_{1-5}$alkyl-CO—NR$^{14}$—$C_{1-5}$alkyl- are prepared using the following synthesis scheme. The intermediates of formula (IV$^b$) are obtained as described hereinbefore. Deprotection and subsequent formation of the corresponding ether using the appropriate aminated alcohol under standard conditions provides the intermediates of formula (XXVIII). Deprotection followed by ring closure provides the target compounds of formula (I'$^b$).

Scheme 8

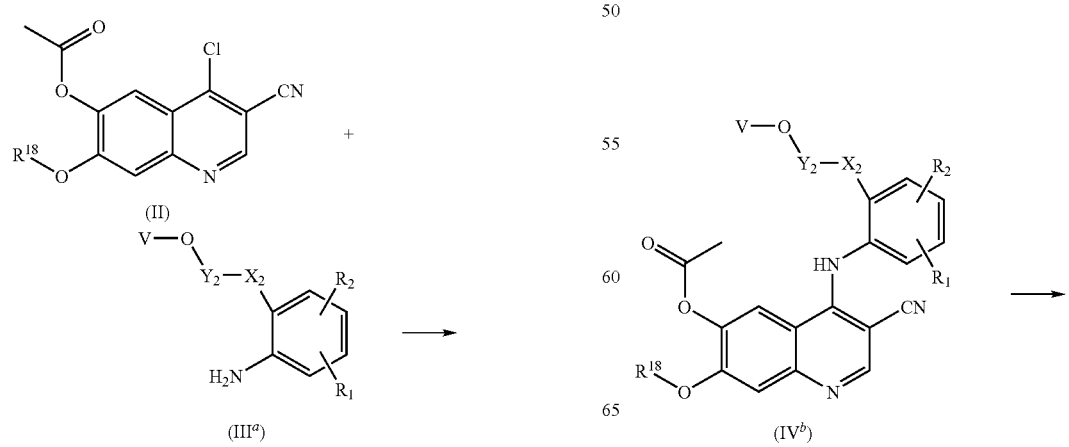

-continued

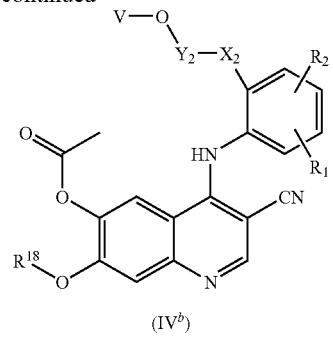

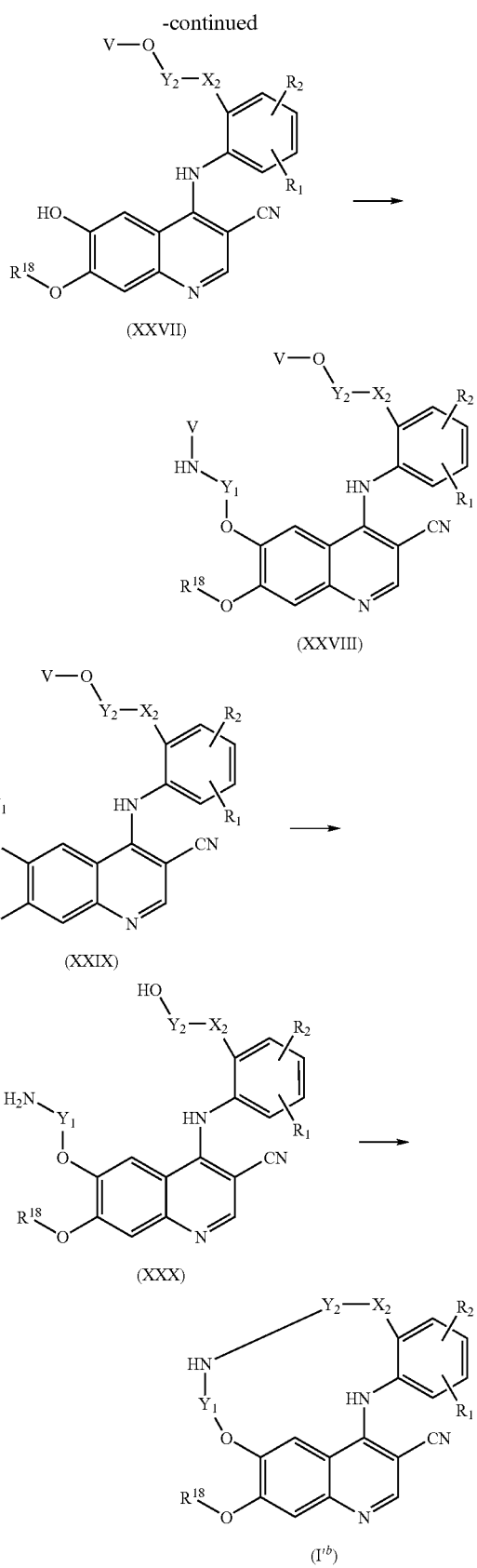

V=protective group such as for example, methylcarbonyl, t-butyl, methyl, ethyl, benzyloxycarbonyl or trialkylsilyl groups, or in case of solid phase chemistry the resin to which the remainder of the molecule is attached $R^{18}$ represents $Ar^4$, $Ar^4$—$C_{1-4}$alkyl, $C_{1-4}$alkyl, $C_{2-6}$alkenyl optionally substituted with $Het^{12}$ or $R^{18}$ represents $C_{1-4}$alkyl substituted with one or where possible two or more substituents selected from hydroxy, halo, $Het^2$, $NR^6R^7$, $NR^8R^9$-carbonyl or $Het^3$-carbonyl, wherein $Ar^3$, $Ar^4$, $Het^{12}$, $Het^2$, $R^6$, $R^7$, $R^8$, $R^9$ and $Het^3$ are defined as for the compounds of formula (I) $Y_1$ and $Y_2$ each independently represent a $C_{1-5}$alkyl, CO—$C_{1-5}$alkyl or CO—$CH_2R^{15}$—NH—

Where necessary or desired, any one or more of the following further steps in any order may be performed:

(i) removing any remaining protecting group(s);
(ii) converting a compound of formula (I) or a protected form thereof into a further compound of formula (I) or a protected form thereof;
(iii) converting a compound of formula (I) or a protected form thereof into a N-oxide, a salt, a quaternary amine or a solvate of a compound of formula (I) or a protected form thereof;
(iv) converting a N-oxide, a salt, a quaternary amine or a solvate of a compound of formula (I) or a protected form thereof into a compound of formula (I) or a protected form thereof;
(v) converting a N-oxide, a salt, a quaternary amine or a solvate of a compound of formula (I) or a protected form thereof into another N-oxide, a pharmaceutically acceptable addition salt a quaternary amine or a solvate of a compound of formula (I) or a protected form thereof;
(vi) where the compound of formula (I) is obtained as a mixture of (R) and (S) enantiomers resolving the mixture to obtain the desired enantiomer.

Compounds of formula (I), N-oxides, addition salts, quaternary amines and stereochemical isomeric forms thereof can be converted into further compounds according to the invention using procedures known in the art.

It will be appreciated by those skilled in the art that in the processes described above the functional groups of intermediate compounds may need to be blocked by protecting groups.

Functional groups, which it is desirable to protect, include hydroxy, amino and carboxylic acid. Suitable protecting groups for hydroxy include trialkylsilyl groups (e.g. tert-butyldimethylsilyl, tert-butyldiphenylsilyl or trimethylsilyl), benzyl and tetrahydropyranyl. Suitable protecting groups for amino include tert-butyloxycarbonyl or benzyloxycarbonyl. Suitable protecting groups for carboxylic acid include $C_{(1-6)}$alkyl or benzyl esters.

The protection and deprotection of functional groups may take place before or after a reaction step.

Additionally, the N-atoms in compounds of formula (I) can be methylated by art-known methods using $CH_3$—I in a suitable solvent such as, for example 2-propanone, tetrahydrofuran or dimethylformamide.

The compounds of formula (I) can also be converted into each other following art-known procedures of functional group transformation of which some examples are mentioned hereinafter.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with 3-phenyl-2-(phenylsulfonyl)oxaziridine or with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g. counter-current distribution, liquid chromatography and the like.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

Some of the intermediates and starting materials as used in the reaction procedures mentioned hereinabove are known compounds and may be commercially available or may be prepared according to art-known procedures. However, in the synthesis of macrocyclic kinase inhibitors, such as for example the compounds of formula (I), the present invention further provides;

a) the intermediates of formula (III)

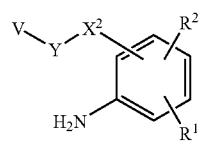

(III)

the pharmaceutically acceptable addition salts and the stereochemically isomeric forms thereof, wherein Y represents —$C_{3-9}$alkyl-, —$C_{3-9}$alkenyl-, —$C_{1-5}$alkyl-oxy-$C_{1-5}$alkyl-, —$C_{1-5}$alkyl-$NR^{12}$—$C_{1-5}$alkyl-, —$C_{1-5}$alkyl-$NR^{13}$—CO—$C_{1-5}$alkyl-, —$C_{1-5}$alkyl-CO—$NR^{14}$—$C_{1-5}$alkyl-, —$C_{1-5}$alkyl-CO—NH—, —$C_{1-6}$alkyl-NH—CO—, —$C_{1-7}$alkyl-CO—, $C_{1-6}$alkyl-CO—$C_{1-6}$alkyl;

$X^2$ represents a direct bond, O, —O—$C_{1-2}$alkyl-, CO, —CO—$C_{1-2}$alkyl-, $NR^{11}$, —$NR^{11}$—$C_{1-2}$alkyl-, —$CH_2$—, —O—N=CH— or $C_{1-2}$alkyl;

$R^1$ represents hydrogen, cyano, halo, hydroxy, formyl, $C_{1-6}$alkoxy-, $C_{1-6}$alkyl-, $C_{1-6}$alkoxy- substituted with halo, $C_{1-4}$alkyl substituted with one or where possible two or more substituents selected from hydroxy or halo; and $R^2$ represents hydrogen, cyano, halo, hydroxy, hydroxycarbonyl-, $Het^{16}$-carbonyl-, $C_{1-4}$alkyloxycarbonyl-, $C_{1-4}$alkylcarbonyl-, aminocarbonyl-, mono- or di($C_{1-4}$alkyl)aminocarbonyl-, $Het^1$, formyl, $C_{1-4}$alkyl-, $C_{2-6}$alkynyl-, $C_{3-6}$cycloalkyl-, $C_{3-6}$cycloalkyloxy-, $C_{1-6}$alkoxy-, $Ar^5$, $Ar^1$-oxy-, dihydroxyborane, $C_{1-6}$alkoxy- substituted with halo, $C_{1-4}$alkyl substituted with one or where possible two or more substituents selected from halo, hydroxy or $NR^4R^5$, $C_{1-4}$alkylcarbonyl- wherein said $C_{1-4}$alkyl is optionally substituted with one or where possible two or more substituents selected from hydroxy or $C_{1-4}$alkyl-oxy-;

$R^4$ and $R^5$ are each independently selected from hydrogen or $C_{1-4}$alkyl;

$R^{11}$ represents hydrogen, $C_{1-4}$alkyl, $C_{1-4}$alkyl-oxy-carbonyl-, $Het^{17}$, $Het^{18}$-$C_{1-4}$alkyl-, $C_{2-4}$alkenylcarbonyl- optionally substituted with $Het^{19}$-$C_{1-4}$alkylaminocarbonyl-, $C_{2-4}$alkenylsulfonyl-, $C_{1-4}$alkyloxy$C_{1-4}$alkyl- or phenyl optionally substituted with one or where possible two or more substituents selected from hydrogen, hydroxy, amino or $C_{1-4}$alkyloxy-;

$R^{12}$ represents hydrogen, $C_{1-4}$alkyl, $Het^{13}$, $Het^{14}$-$C_{1-4}$alkyl- or phenyl optionally substituted with one or where possible two or more substituents selected from hydrogen, hydroxy, amino or $C_{1-4}$alkyloxy-;

$R^{13}$ and $R^{14}$ are each independently selected from hydrogen, $C_{1-4}$alkyl, $Het^{15}$-$C_{1-4}$alkyl- or $C_{1-4}$alkyloxy$C_{1-4}$alkyl-;

$Het^1$ represents a heterocycle selected from piperidinyl, morpholinyl, piperazinyl, furanyl, pyrazolyl, dioxolanyl, thiazolyl, oxazolyl, imidazolyl, isoxazolyl, oxadiazolyl, pyridinyl or pyrrolidinyl wherein said $Het^1$ is optionally substituted amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl- mono- or di($C_{1-4}$alkyl)amino- or amino-carbonyl-;

$Het^{13}$ represent a heterocycle selected from pyrrolidinyl or piperidinyl wherein said heterocycle is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{14}$ represent a heterocycle selected from morpholinyl, pyrrolidinyl, piperazinyl or piperidinyl wherein said $Het^{14}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{15}$ represent a heterocycle selected from morpholinyl, pyrrolidinyl, piperazinyl or piperidinyl wherein said $Het^{15}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{16}$ represent a heterocycle selected from morpholinyl, pyrrolidinyl, piperazinyl, 1,3,2-dioxaborolane or piperidinyl wherein said heterocycle is optionally substituted with one or more substituents selected from $C_{1-4}$alkyl; and $Het^{17}$ represent a heterocycle selected from pyrrolidinyl or piperidinyl wherein said heterocycle is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

Het$^{18}$ and Het$^{19}$ each independently represent a heterocycle selected from morpholinyl, pyrrolidinyl, piperazinyl or piperidinyl wherein said Het$^{18}$ and Het$^{19}$ are optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

Ar$^1$, Ar$^2$, Ar$^3$, Ar$^4$ and Ar$^5$ each independently represent phenyl optionally substituted with cyano, $C_{1-4}$alkylsulfonyl-, $C_{1-4}$alkylsulfonylamino-, aminosulfonylamino-, hydroxy-$C_{1-4}$alkyl, aminosulfonyl-, hydroxy-, $C_{1-4}$alkyloxy- or $C_{1-4}$alkyl.

In particular the intermediates of formula (III) wherein one or more of the following restrictions apply;

i) Y represents —$C_{3-9}$alkyl-, —$C_{1-5}$alkyl-oxy-$C_{1-5}$alkyl-, —$C_{1-5}$alkyl-NR$^{12}$—$C_{1-5}$alkyl-, —$C_{1-6}$alkyl-NH—CO—;

ii) X$^2$ represents a direct bond, O, —O—$C_{1-2}$alkyl-, NR$^{11}$, —NR$^{11}$—$C_{1-2}$alkyl-, —CH$_2$—, —O—N=CH— or $C_{1-2}$alkyl;

iii) R$^1$ represents hydrogen, cyano, halo or hydroxy, preferably halo;

iv) R$^2$ represents hydrogen, cyano, halo, hydroxy, hydroxycarbonyl-, $C_{1-4}$alkyloxycarbonyl-, Het$^{16}$-carbonyl-, $C_{1-4}$alkyl-, $C_{2-6}$alkynyl-, Ar$^5$ or Het$^1$; In a further embodiment R$^2$ represents hydrogen, cyano, halo, hydroxy, $C_{2-6}$alkynyl- or Het$^1$; in particular R$^2$ represents hydrogen, cyano, halo, hydroxy, or Ar$^5$;

v) R$^{11}$ represents hydrogen, $C_{1-4}$alkyl, or $C_{1-4}$alkyloxycarbonyl;

vi) R$^{12}$ represents Het$^{14}$-$C_{1-4}$alkyl, in particular morpholinyl-$C_{1-4}$alkyl;

vii) Het$^1$ represents thiazolyl optionally substituted with amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl- mono- or di($C_{1-4}$alkyl)amino- or amino-carbonyl-;

viii) Het$^{16}$ represents a heterocycle selected from piperidinyl or pyrrolidinyl.

b) the intermediates of formula (XXX)

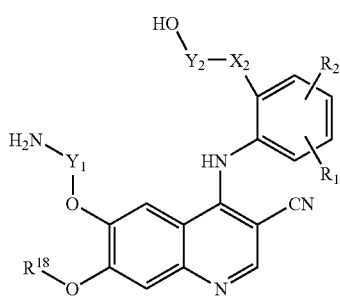

(XXX)

the pharmaceutically acceptable addition salts and the stereochemically isomeric forms thereof, wherein Y$_i$ and Y$_2$ each independently represent $C_{1-5}$alkyl, CO—$C_{1-5}$alkyl or CO—CH$_2$R$^{15}$—NH—;

X$^1$ represents a direct bond, O, —O—$C_{1-2}$alkyl-, CO, —CO—$C_{1-2}$alkyl-, —NH—, —NR$^{10}$—$C_{1-2}$alkyl-, —CH$_2$—, —O—N=CH— or —$C_{1-2}$alkyl-;

X$^2$ represents a direct bond, O, —O—$C_{1-2}$alkyl-, CO, —CO—$C_{1-2}$alkyl-, NR$^{11}$, —NR$^{11}$—$C_{1-2}$alkyl-, —CH$_2$—, —O—N=CH— or $C_{1-2}$alkyl;

R$^1$ represents hydrogen, cyano, halo, hydroxy, formyl, $C_{1-6}$alkoxy-, $C_{1-6}$alkyl-, $C_{1-6}$alkoxy- substituted with halo, $C_{1-4}$alkyl substituted with one or where possible two or more substituents selected from hydroxy or halo; and R$^2$ represents hydrogen, cyano, halo, hydroxy, hydroxycarbonyl-, Het$^{16}$-carbonyl-, $C_{1-4}$alkyloxycarbonyl-, $C_{1-4}$alkylcarbonyl-, aminocarbonyl-, mono- or di($C_{1-4}$alkyl)aminocarbonyl-, Het$^1$, formyl, $C_{1-4}$alkyl-, $C_{2-6}$alkynyl-, $C_{3-6}$cycloalkyl, $C_{3-6}$cycloalkyloxy-, $C_{1-6}$alkoxy-, Ar$^5$, Ar$^1$-oxy-, dihydroxyborane, $C_{1-6}$alkoxy- substituted with halo, $C_{1-4}$alkyl substituted with one or where possible two or more substituents selected from halo, hydroxy or NR$^4$R$^5$, $C_{1-4}$alkylcarbonyl- wherein said $C_{1-4}$alkyl is optionally substituted with one or where possible two or more substituents selected from hydroxy or $C_{1-4}$alkyl-oxy-;

R$^4$ and R$^5$ are each independently selected from hydrogen or $C_{1-4}$alkyl;

R$^6$ and R$^7$ are each independently selected from hydrogen, $C_{1-4}$alkyl, Het$^8$, aminosulfonyl-, mono- or di ($C_{1-4}$alkyl)-aminosulfonyl, hydroxy-$C_{1-4}$alkyl-, $C_{1-4}$alkyl-oxy-$C_{1-4}$alkyl-, hydroxycarbonyl-$C_{1-4}$alkyl-, $C_{3-6}$cycloalkyl, Het$^9$-carbonyl-$C_{1-4}$alkyl-, Het$^{10}$-carbonyl-, polyhydroxy-$C_{1-4}$alkyl-, Het$^{11}$-$C_{1-4}$alkyl- or Ar$^2$—$C_{1-4}$alkyl-;

R$^8$ and R$^9$ are each independently selected from hydrogen, $C_{1-4}$alkyl, $C_{3-6}$cycloalkyl, Het$^4$, hydroxy-$C_{1-4}$alkyl-, $C_{1-4}$alkyloxy$C_{1-4}$alkyl- or polyhydroxy-$C_{1-4}$alkyl-;

R$^{10}$ represents hydrogen, $C_{1-4}$alkyl, $C_{1-4}$alkyl-oxy-carbonyl-, Het$^{17}$, Het$^{18}$-$C_{1-4}$alkyl-, $C_{2-4}$alkenylcarbonyl- optionally substituted with Het$^{19}$-$C_{1-4}$alkylaminocarbonyl-, $C_{2-4}$alkenylsulfonyl-, $C_{1-4}$alkyloxy$C_{1-4}$alkyl- or phenyl optionally substituted with one or where possible two or more substituents selected from hydrogen, hydroxy, amino or $C_{1-4}$alkyloxy-;

R$^{11}$ represents hydrogen, $C_{1-4}$alkyl, Het$^{13}$, Het$^{14}$-$C_{1-4}$alkyl- or phenyl optionally substituted with one or where possible two or more substituents selected from hydrogen, hydroxy, amino or $C_{1-4}$alkyloxy-;

R$^{18}$ represents Ar$^3$, Ar$^4$—$C_{1-4}$alkyl, $C_{1-4}$alkyl, $C_{2-6}$alkenyl optionally substituted with Het$^{12}$ or R$^{18}$ represents $C_{1-4}$alkyl substituted with one or where possible two or more substituents selected from $C_{1-4}$alkyloxy, hydroxy, halo, Het$^2$, NR$^6$R$^7$, NR$^8$R$^9$-carbonyl or Het$^3$-carbonyl;

R$^{15}$ represents hydrogen or $C_{1-4}$alkyl optionally substituted with phenyl, indolyl, methylsulfide, hydroxy, thiol, hydroxyphenyl, aminocarbonyl, hydroxycarbonyl, amine, imidazoyl or guanidino;

Het$^1$ represents a heterocycle selected from piperidinyl, morpholinyl, piperazinyl, furanyl, pyrazolyl, dioxolanyl, thiazolyl, oxazolyl, imidazolyl, isoxazolyl, oxadiazolyl, pyridinyl or pyrrolidinyl wherein said Het$^1$ is optionally substituted amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl- mono- or di($C_{1-4}$alkyl)amino- or amino-carbonyl-;

Het$^2$ represents a heterocycle selected from morpholinyl, piperazinyl, piperidinyl, pyrrolidinyl, thiomorpholinyl or dithianyl wherein said Het$^2$ is optionally substituted with one or where possible two or more substituents selected from hydroxy, halo, amino, $C_{1-4}$alkyl-, hydroxy-$C_{1-4}$alkyl-, $C_{1-4}$alkyl-oxy-$C_{1-4}$alkyl-, hydroxy-$C_{1-4}$alkyl-oxy-$C_{1-4}$alkyl-, mono- or di($C_{1-4}$alkyl)amino-, mono- or di($C_{1-4}$alkyl)amino-$C_{1-4}$alkyl-, amino$C_{1-4}$alkyl-, mono- or di($C_{1-4}$alkyl)amino-sulfonyl-, aminosulfonyl-;

Het$^3$, Het$^4$ and Het$^8$ each independently represent a heterocycle selected from morpholinyl, piperazinyl, piperidinyl, furanyl, pyrazolyl, dioxolanyl, thiazolyl, oxazolyl, imidazolyl, isoxazolyl, oxadiazolyl, pyridinyl or pyrrolidinyl wherein said $Het^3$, $Het^4$ or $Het^8$ is optionally substituted with one or where possible two or more substituents selected from hydroxy-, amino-, $C_{1-4}$alkyl-, $C_{3-6}$cycloalkyl-$C_{1-4}$alkyl-, aminosulfonyl-, mono- or di($C_{1-4}$alkyl)aminosulfonyl or amino-$C_{1-4}$alkyl-;

$Het^9$ and $Het^{10}$ each independently represent a heterocycle selected from furanyl, piperidinyl, morpholinyl, piperazinyl, pyrazolyl, dioxolanyl, thiazolyl, oxazolyl, imidazolyl, isoxazolyl, oxadiazolyl, pyridinyl or pyrrolidinyl wherein said $Het^9$ or $Het^{10}$ is optionally substituted $C_{1-4}$alkyl, $C_{3-6}$cycloalkyl-$C_{1-4}$alkyl- or amino-$C_{1-4}$alkyl-;

$Het^{11}$ represents a heterocycle selected from indolyl or

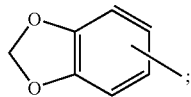

$Het^{12}$ represents a heterocycle selected from morpholinyl, piperazinyl, piperidinyl, pyrrolidinyl, thiomorpholinyl or dithianyl wherein said $Het^{12}$ is optionally substituted with one or where possible two or more substituents selected from hydroxy, halo, amino, $C_{1-4}$alkyl-, hydroxy-$C_{1-4}$alkyl-, $C_{1-4}$alkyl-oxy-$C_{1-4}$alkyl-, hydroxy-$C_{1-4}$alkyl-oxy-$C_{1-4}$alkyl-, mono- or di($C_{1-4}$alkyl)amino- or mono- or di($C_{1-4}$alkyl)amino-$C_{1-4}$alkyl-;

$Het^{13}$ represent a heterocycle selected from pyrrolidinyl or piperidinyl wherein said $Het^{13}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{14}$ represent a heterocycle selected from morpholinyl, pyrrolidinyl, piperazinyl or piperidinyl wherein said heterocycle is optionally substituted with one or where possible two or more substituents selected from $C_{1-4}$alkyl, $C_{3-6}$cycloalkyl, hydroxy-$C_{1-4}$allkyl-, $C_{1-4}$alkyloxy$C_{1-4}$alkyl or polyhydroxy-$C_{1-4}$alkyl-;

$Het^{16}$ represent a heterocycle selected from morpholinyl, pyrrolidinyl, piperazinyl, 1,3,2-dioxaborolane or piperidinyl wherein said heterocycle is optionally substituted with one or more substituents selected from $C_{1-4}$alkyl; and $Het^{17}$ represent a heterocycle selected from pyrrolidinyl or piperidinyl wherein said heterocycle is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{18}$ and $Het^{19}$ each independently represent a heterocycle selected from morpholinyl, pyrrolidinyl, piperazinyl or piperidinyl wherein said $Het^{18}$ and $Het^{19}$ are optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Ar^1$, $Ar^3$, $Ar^4$ and $Ar^5$ each independently represent phenyl optionally substituted with cyano, $C_{1-4}$alkylsulfonyl-, $C_{1-4}$alkylsulfonylamino-, aminosulfonylamino-, hydroxy-$C_{1-4}$alkyl, aminosulfonyl-, hydroxy-, $C_{1-4}$alkyloxy- or $C_{1-4}$alkyl.

In particular those intermediates of formula (XXX) wherein one or more of the following restrictions apply;
i) $X^1$ represents —O—;
ii) $X^2$ represents a direct bond, —$NR^{11}$—$C_{1-2}$alkyl-, —$NR^{11}$—$CH_2$—, —$C_{1-2}$alkyl-, —O—$C_{1-2}$alkyl-, —O— or —O—$CH_2$—;
iii) $R^1$ represents hydrogen or halo;
iv) $R^2$ represents hydrogen, cyano, halo, hydroxycarbonyl-, $C_{1-4}$alkyloxycarbonyl-, $Het^{16}$-carbonyl- or $Ar^5$;
v) $R^{18}$ represents hydrogen, $C_{1-4}$alkyl-, $Ar^4$—$C_{1-4}$alkyl or $R^{18}$ represents $C_{1-4}$alkyl substituted with one or where possible two or more substituents selected from $C_{1-4}$alkyloxy- or $Het^2$-;
vi) $R^{11}$ represents hydrogen, $C_{1-4}$alkyl- or $C_{1-4}$alkyl-oxy-carbonyl-;
vii) $R^{12}$ represents $Het^{14}$-$C_{1-4}$alkyl, in particular morpholinyl-$C_{1-4}$alkyl;
viii) $Het^2$ represents a heterocycle selected from morpholinyl, piperazinyl, piperidinyl or pyrrolidinyl wherein said $Het^2$ is optionally substituted with one or where possible two or more substituents selected from hydroxy, amino or $C_{1-4}$alkyl-;
In a further embodiment $Het^2$ represents a heterocycle selected from morpholinyl or piperidinyl optionally substituted with $C_{1-4}$alkyl-, preferably methyl;
ix) $Het^{14}$ represents morpholinyl;
x) $Het^{16}$ represents a heterocycle selected from morpholinyl or pyrrolidinyl;
xi) $Ar^4$ represents phenyl;
xii) $Ar^5$ represents phenyl optionally substituted with cyano.

It is also an object of the present invention to provide the use of an intermediate of formula (III) or (XXX) in the synthesis of a compound of formula (I).

The compounds of the present invention are useful because they possess pharmacological properties. They can therefore be used as medicines.

As described in the experimental part hereinafter, the growth inhibitory effect and anti-tumour activity of the present compounds has been demonstrated in vitro, in enzymatic assays on the receptor tyrosine kinase EGFR. In an alternative assay, the growth inhibitory effect of the compounds was tested on the ovarian carcinoma cell line SKOV3 using art known cytotoxicity assays such as LIVE/DEAD (Molecular Probes) or MTT.

Accordingly, the present invention provides the compounds of formula (I) and their pharmaceutically acceptable N-oxides, addition salts, quaternary amines and stereochemically isomeric forms for use in therapy. More particular in the treatment or prevention of cell proliferation mediated diseases. The compounds of formula (I) and their pharmaceutically acceptable N-oxides, addition salts, quaternary amines and the stereochemically isomeric forms may hereinafter be referred to as compounds according to the invention.

Disorders for which the compounds according to the invention are particularly useful are atherosclerosis, restenosis, cancer and diabetic complications e.g. retinopathy.

In view of the utility of the compounds according to the invention, there is provided a method for the treatment of an animal, for example, a mammal including humans, suffering from a cell proliferative disorder such as atherosclerosis, restenosis and cancer, which comprises administering an effective amount of a compound according to the present invention.

Said method comprising the systemic or topical administration of an effective amount of a compound according to the invention, to animals, including humans.

Due to their high degree of selectivity as EGFR inhibitors, the compounds of formula (I) as defined above, are also useful to mark or identify the kinase domain within the receptor tyrosine kinase receptors. To this purpose, the compounds of the present invention can be labelled, in particular by replacing, partially or completely, one or more atoms in the molecule by their radioactive isotopes. Examples of interesting labelled compounds are those compounds having at least one halo which is a radioactive isotope of iodine, bromine or fluorine; or those compounds having at least one $^{11}$C-atom or tritium atom.

One particular group consists of those compounds of formula (I) wherein $R^1$ is a radioactive halogen atom. In principle, any compound of formula (I) containing a halogen atom is prone for radiolabeling by replacing the halogen atom by a suitable isotope. Suitable halogen radioisotopes to this purpose are radioactive iodides, e.g. $^{122}$I, $^{123}$I, $^{125}$I, $^{131}$I; radioactive bromides, e.g. $^{75}$Br, $^{76}$Br, $^{77}$Br and $^{82}$Br, and radioactive fluorides, e.g. $^{18}$F. The introduction of a radioactive halogen atom can be performed by a suitable exchange reaction or by using any one of the procedures as described hereinabove to prepare halogen derivatives of formula (I).

Another interesting form of radiolabeling is by substituting a carbon atom by a $^{11}$C-atom or the substitution of a hydrogen atom by a tritium atom.

Hence, said radiolabelled compounds of formula (I) can be used in a process of specifically marking receptor sites in biological material. Said process comprises the steps of (a) radiolabeling a compound of formula (I), (b) administering this radio-labelled compound to biological material and subsequently (c) detecting the emissions from the radiolabelled compound.

The term biological material is meant to comprise every kind of material which has a biological origin. More in particular this term refers to tissue samples, plasma or body fluids but also to animals, specially warm-blooded animals, or parts of animals such as organs.

When used in in vivo assays, the radiolabelled compounds are administered in an appropriate composition to an animal and the location of said radiolabelled compounds is detected using imaging techniques, such as, for instance, Single Photon Emission Computerized Tomography (SPECT) or Positron Emission Tomography (PET) and the like. In this manner the distribution of the particular receptor sites throughout the body can be detected and organs containing said receptor sites can be visualized by the imaging techniques mentioned hereinabove. This process of imaging an organ by administering a radiolabelled compound of formula (I) and detecting the emissions from the radioactive compound also constitutes a part of the present invention.

In yet a further aspect, the present invention provides the use of the compounds according to the invention in the manufacture of a medicament for treating any of the aforementioned cell proliferative disorders or indications.

The amount of a compound according to the present invention, also referred to here as the active ingredient, which is required to achieve a therapeutic effect will be, of course, vary with the particular compound, the route of administration, the age and condition of the recipient, and the particular disorder or disease being treated. A suitable daily dose would be from 0.01 mg/kg to 300 mg/kg body weight, in particular from 10 mg/kg to 100 mg/kg body weight. A method of treatment may also include administering the active ingredient on a regimen of between one and four intakes per day.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

EXPERIMENTAL PART

Hereinafter, the term "ADDP" is defined as 1,1'-(azodicarbonyl)bis-piperidine, "BuLi" is defined as butyl-lithium, "DCM" is defined as dichloromethane, "DIPE" is defined as diisopropyl ether, "DMF" is defined as N,N-dimethylformamide, "MeOH" is defined as methanol, "THF" is defined as tetrahydrofuran, "iPrOH" is defined as 2-propanol, "t-BuOH" is defined as 2-methyl-2-butanol, "AcOEt" is defined as ethyl acetate, "TFA" is defined as trifluoroacetic acid, "DIPEA" is defined as diisopropylethylamine "HBTU" is defined as 1-[bis(dimethylamino)methylene]-, hexafluorophosphate(1-), 1H-benzotriazolium, 3-oxide, "(n-Bu)₄NI" is defined as tetrabutylammonium iodide, "NMP" is defined as 1-methyl-2-pyrrolidinone and "Et₃N" is defined as N,N-diethylethanamine Example O1

General Description for the Synthesis of Compounds of Formula 12

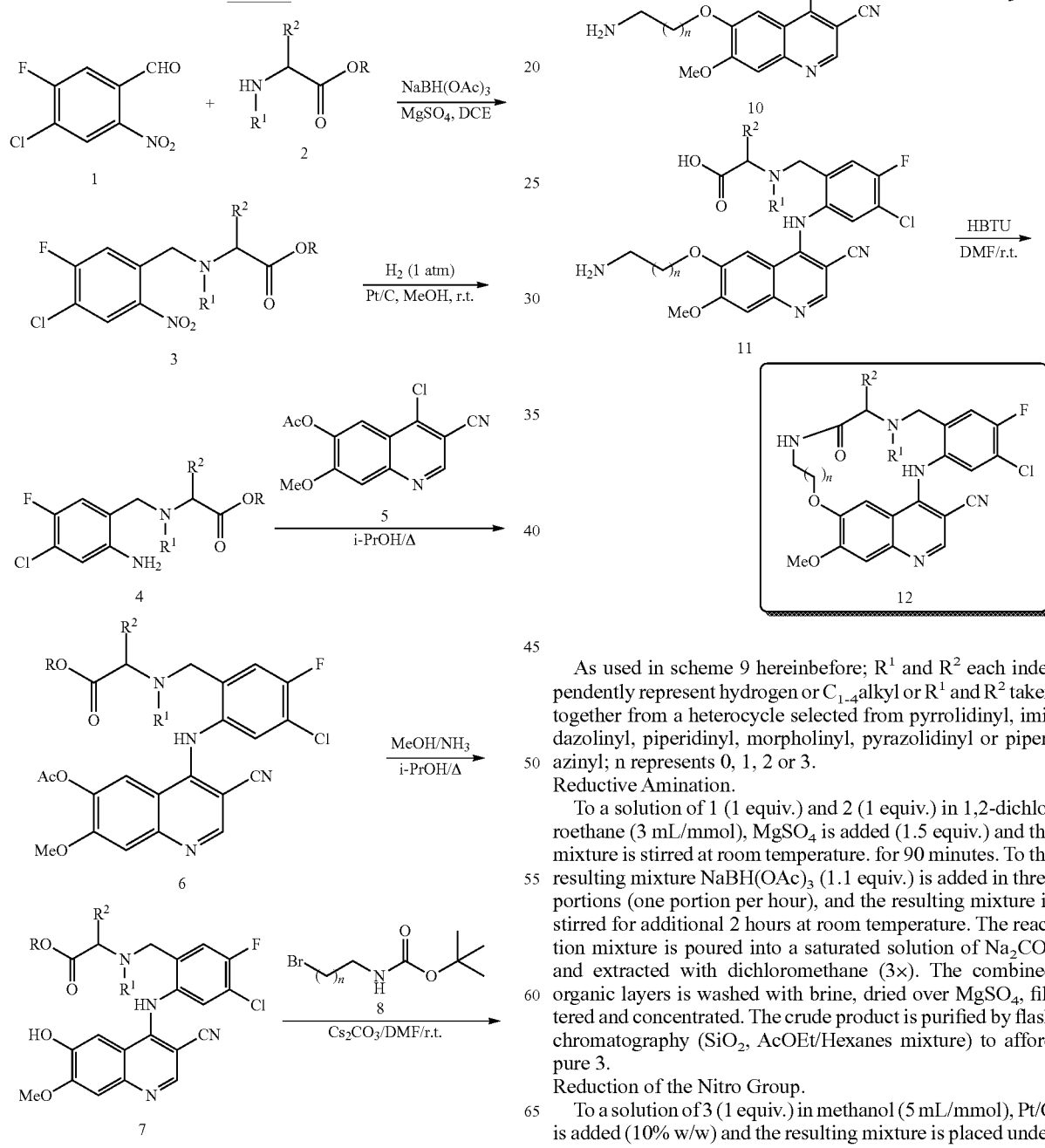

As used in scheme 9 hereinbefore; $R^1$ and $R^2$ each independently represent hydrogen or $C_{1-4}$alkyl or $R^1$ and $R^2$ taken together from a heterocycle selected from pyrrolidinyl, imidazolinyl, piperidinyl, morpholinyl, pyrazolidinyl or piperazinyl; n represents 0, 1, 2 or 3.

Reductive Amination.

To a solution of 1 (1 equiv.) and 2 (1 equiv.) in 1,2-dichloroethane (3 mL/mmol), MgSO₄ is added (1.5 equiv.) and the mixture is stirred at room temperature. for 90 minutes. To the resulting mixture NaBH(OAc)₃ (1.1 equiv.) is added in three portions (one portion per hour), and the resulting mixture is stirred for additional 2 hours at room temperature. The reaction mixture is poured into a saturated solution of Na₂CO₃ and extracted with dichloromethane (3×). The combined organic layers is washed with brine, dried over MgSO₄, filtered and concentrated. The crude product is purified by flash chromatography (SiO₂, AcOEt/Hexanes mixture) to afford pure 3.

Reduction of the Nitro Group.

To a solution of 3 (1 equiv.) in methanol (5 mL/mmol), Pt/C is added (10% w/w) and the resulting mixture is placed under H₂ atmosphere (balloon) and stirred at room temperature overnight (14 hours). The mixture is filtered through a short pad of celite and concentrated to dryness. In certain cases purification through flash chromatography is required to afford pure anilines of type 4.

Nucleophilic Displacement.

To a stirred suspension of chlorocyano quinoline 5 (1.05 equiv) in iPrOH or t-BuOH (11 mL/mmol), 4 is added (1 equiv.). The mixture is allowed to react under reflux temperature under $N_2$ for 6-8 hours. The reaction mixture is evaporated to dryness and the resulting residue is purified by flash-chromatography ($SiO_2$, AcOEt/Hexanes mixture) to afford pure 6.

Deacetylation.

Compound 6 is dissolved in $MeOH/NH_3$ 7N (8 mL/mmol). To this solution, iPrOH (2 mL/mmol) is added and the reaction mixture stirred at room temperature for 30-120 minutes (TLC monitoring). The mixture is concentrated to dryness and the resulting product used in the next step without further purification.

Alkylation Reaction.

To a stirred solution of 7 in DMF (5 mL/mmol), $Cs_2CO_3$ (3 equiv.) is added followed by the alkylating reagent (2.5 equiv.). The reaction mixture is stirred at room temperature overnight. When necessary, an additional 3 equiv. of $Cs_2CO_3$ and 2.5 equiv. of the alkylating reagent is added and the reaction mixture further stirred at room temperature until total completion of the reaction (TLC monitoring). The reaction mixture is partitioned between brine and AcOEt, and the layers separated. The organic layer is dried over $MgSO_4$, filtered and evaporated. The residue is purified by flash-chromatography (AcOEt/n-hexanes) to afford pure 9.

Cleavage of the Boc Group.

To a cooled (0° C.) solution of 9 in $CH_2Cl_2$ (3 mL/mmol), TFA (2 mL/mmol) is added dropwise. The resulting mixture is warmed to room temperature and stirred for 1-2 hours. A saturated solution of $NaHCO_3$ is added to the reaction mixture until basic pH is reached. The mixture is extracted with $CH_2Cl_2$ (2×). The combined organic layers are dried over $MgSO_4$, filtered and concentrated to dryness. The resulting free amine is obtained with enough purity to be used in the next step without further purification.

Saponification of the Ester Group.

To a solution of 10 in $MeOH/H_2O$ (10:1) is added $LiOH.H_2O$ (5 equiv.) and the reaction mixture is stirred at room temperature up to 2 hours. The solvent is evaporated under vaccuo and the residue is dissolved in DMF and filtered through a syntered glass funnel. The DMF is removed and the product used as such in the following reaction.

Cyclization Reaction.

A solution of 11 (0.25 mmol, 1 equiv.) and DIPEA (6 equiv) in DMF (10 mL) are added dropwise to a solution of HBTU (3 equiv) in DMF (100 mL/mmol of 11). The resulting mixture is stirred at room temperature for 1 hour. The solvent is evaporated and the product purified by reverse-phase HPLC.

By the above synthetic procedures, the following compounds are obtained:

7-chloro-8-fluoro-21-methoxy-13-oxo-10,11,12,13,14,15,16,17-octahydro-5H-1,19-(ethanediylidene)pyrido[4,3-b][6,1,10,13]benzoxatriazacyclohexadecine-4-carbonitrile (compound 1.1)

20-chloro-19-fluoro-23-methoxy-12-oxo-9,10,11,12,12a,13,14,15,17,22-decahydro-8H-4,6-(ethanediylidene)pyrido[4,3-b]pyrrolo[2,1-l][6,1,10,13]benzoxatriazacyclohexadecine-1-carbonitrile (compound 1.2)

7-chloro-8-fluoro-21-methoxy-11-methyl-13-oxo-10,11,12,13,14,15,16,17-octahydro-5H-1,19-(ethanediylidene)pyrido[4,3-b][6,1,10,13]benzoxatriazacyclohexadecine-4-carbonitrile (compound 1.3)

17-chloro-16-fluoro-20-methoxy-13-methyl-11-oxo-8,9,10,11,12,13,14,19-octahydro-4,6-(ethanediylidene)pyrido[4,3-b][6,1,9,12]benzoxatriazacyclopentadecine-1-carbonitrile (compound 1.4)

7-chloro-8-fluoro-12-isobutyl-21-methoxy-13-oxo-10,11,12,13,14,15,16,17-octahydro-5H-1,19-(ethanediylidene)pyrido[4,3-b][6,1,10,13]benzoxatriazacyclohexadecine-4-carbonitrile (compound 1.5)

Example O2

General Description for the Synthesis of Compounds of Formula 13

Scheme 10

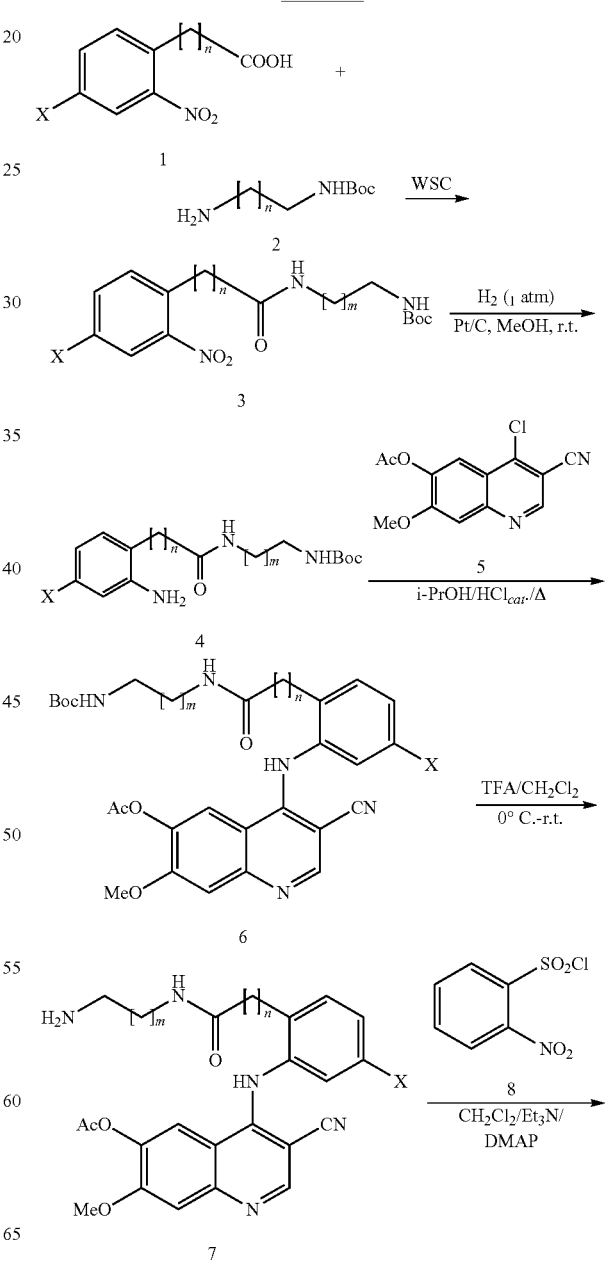

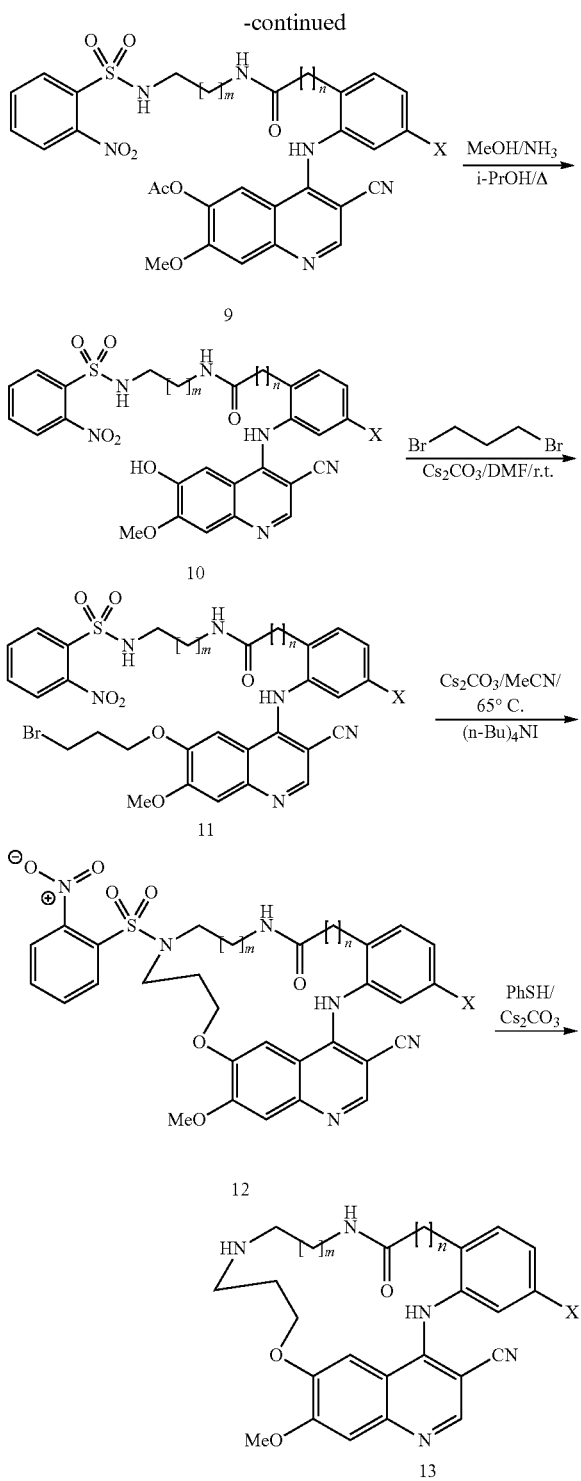

As used in scheme 10 hereinbefore; X represents halo, in particular chloro, fluoro or bromo; n represents 0, 1, 2 or 3; m represents 0, 1, 2 or 3.

Amide Formation.

To a stirred solution of 1 (1 equiv.) in $CH_2Cl_2$ (5 mL/mmol), diisopropyl carbodiimide (1.05 equiv.) is added. The reaction mixture is stirred for 30 minutes at room temperature, then the amine 2 (1.05 equiv.) is added and stirring continued for another 30 minutes. The reaction mixture is then partitioned between 1N citric acid and $CH_2Cl_2$. The layers are separated and the organic layer dried over $MgSO_4$, filtered and evaporated to afford 3 with enough purity to be used in the next step.

Reduction of the Nitro Group.

To a solution of 3 (1 equiv.) in MeOH (5 mL/mmol), Pt/C is added (10% w/w) and the resulting mixture is placed under $H_2$ atmosphere (balloon) and stirred at room temperature overnight (14 hours). The mixture is filtered through a short pad of celite and concentrated to dryness. In certain cases purification through flash chromatography is required to afford pure anilines of type 4.

Nucleophilic Displacement.

To a stirred suspension of chlorocyano quinoline 5 (1.05 equiv.) in iPrOH (11 mL/mmol), 4 is added (1 equiv.) and a few drops of conc. HCl. The mixture is allowed to react under reflux temperature under $N_2$ for 6-8 hours. The reaction mixture is evaporated to dryness and the resulting residue purified by flash-chromatography ($SiO_2$, AcOEt/Hexanes mixture) to afford pure 6.

Cleavage of the Boc Group.

To a cooled (0° C.) solution of 6 in $CH_2Cl_2$ (3 mL/mmol), TFA (2 mL/mmol) is added dropwise. The resulting mixture is allowed to warm to room temperature and stirred for 1-2 hours. A saturated solution of $NaHCO_3$ is added to the reaction mixture until basic pH is reached. The mixture is extracted with $CH_2Cl_2$ (2×). The combined organic layers are dried over $MgSO_4$, filtered and concentrated to dryness. The resulting free amine is obtained with enough purity to be used in the next step without further purification.

Sulfonylation Reaction.

To a cooled (0° C.) solution of 7 (1 equiv.), in $CH_2Cl_2$ (2 mL/mmol), $Et_3N$ (1.5 equiv.), and DMAP (10% mol) are added. A solution of ortho-nitrobenzosulfonyl chloride (1.1 equiv.) in $CH_2Cl_2$ (1 mL/mmol of 7) is added dropwise. The reaction mixture is stirred at 0° C. and allowed to warm to room temperature overnight. 1N HCl is added until acidic pH is reached, and the layers separated. The organic layer is dried over $MgSO_4$, filtered and evaporated. The resulting residue is purified by flash-chromatography (AcOEt/hexanes) to afford pure 9.

Deacetylation.

Compound 9 is dissolved in $MeOH/NH_3$ 7N (8 mL/mmol). To this solution, iPrOH (2 mL/mmol) is added and the reaction mixture stirred at room temperature for 30-120 minutes (TLC monitoring). The mixture is concentrated to dryness and the resulting product used in the next step without further purification.

Alkylation Reaction.

To a stirred solution of 10 in DMF (5 mL/mmol), $Cs_2CO_3$ (3 equiv.) are added followed by the alkylating reagent (2.5 equiv.). The reaction mixture is stirred at room temperature overnight. If necessary, an additional 3 equiv. of $Cs_2CO_3$ and 2.5 equiv. of the alkylating reagent are added and the reaction mixture is stirred at room temperature until total completion of the reaction (TLC monitoring). The reaction mixture is partitioned between brine and AcOEt, and the layers are separated. The organic layer is dried over $MgSO_4$, filtered and evaporated. The residue is purified by flash-chromatography (AcOEt/n-hexanes) to afford pure 11.

Cyclization Reaction.

A solution of 11 (1 equiv.) in MeCN (60 mL/mmol) is added dropwise at room temperature over a mixture of $Cs_2CO_3$ (5 equiv.) and (n-Bu)$_4$NI (2 equiv.) in MeCN (30 mL/mmol). The reaction mixture is stirred at 65° C. overnight. Upon completion of the reaction (LC monitoring), $H_2O$ is added. The resulting precipitate is collected by filtration and washed with $H_2O$. The product is dried under vacuum at 65° C. The solid material is boiled in iPrOH. The solid material is filtered and dried.

Desulfonylation Reaction.

A mixture of 12 (1 equiv.), thiophenol (1.2 equiv) and $Cs_2CO_3$ (3 equiv.) in DMF (45 mL/mmol of 12) is stirred at room temperature for 2 hours. The reaction mixture is quenched with ice-$H_2O$ and extracted with $CH_2Cl_2$/MeOH (90:10). The separated organic layer is dried over $MgSO_4$, filtered and evaporated. The product is purified by reverse-phase HPLC.

By the above synthetic procedures, the following compounds are obtained:

7-bromo-23-methoxy-12-oxo-10,11,12,13,14,15,16,17,18,19-decahydro-5H-1,21-(ethanediylidene)pyrido[4,3-b][6,1,10,13]benzoxatriazacyclooctadecine-4-carbonitrile (compound 1.6)

7-chloro-23-methoxy-11-oxo-10,11,12,13,14,15,16,17,18,19-decahydro-5H-1,21-(ethanediylidene)pyrido[4,3-b][6,1,10,14]benzoxatriazacyclooctadecine-4-carbonitrile (compound 2.1)

7-chloro-24-methoxy-12-oxo-5,10,11,12,13,14,15,16,17,18,19,20-dodecahydro-1,22-(ethanediylidene)pyrido[4,3-b][6,1,10,14]benzoxatriazacyclononadecine-4-carbonitrile (compound 2.2)

7-chloro-23-methoxy-12-oxo-10,11,12,13,14,15,16,17,18,19-decahydro-5H-1,21-(ethanediylidene)pyrido[4,3-b][6,1,10,13]benzoxatriazacyclooctadecine-4-carbonitrile (compound 2.4)

Example O3

General Description for the Synthesis of Compounds of Formula 8

Scheme 11

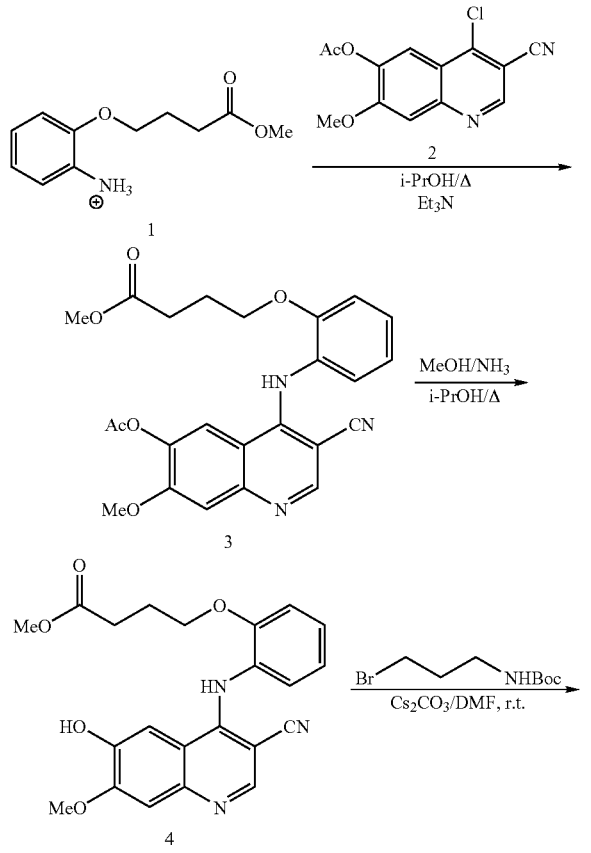

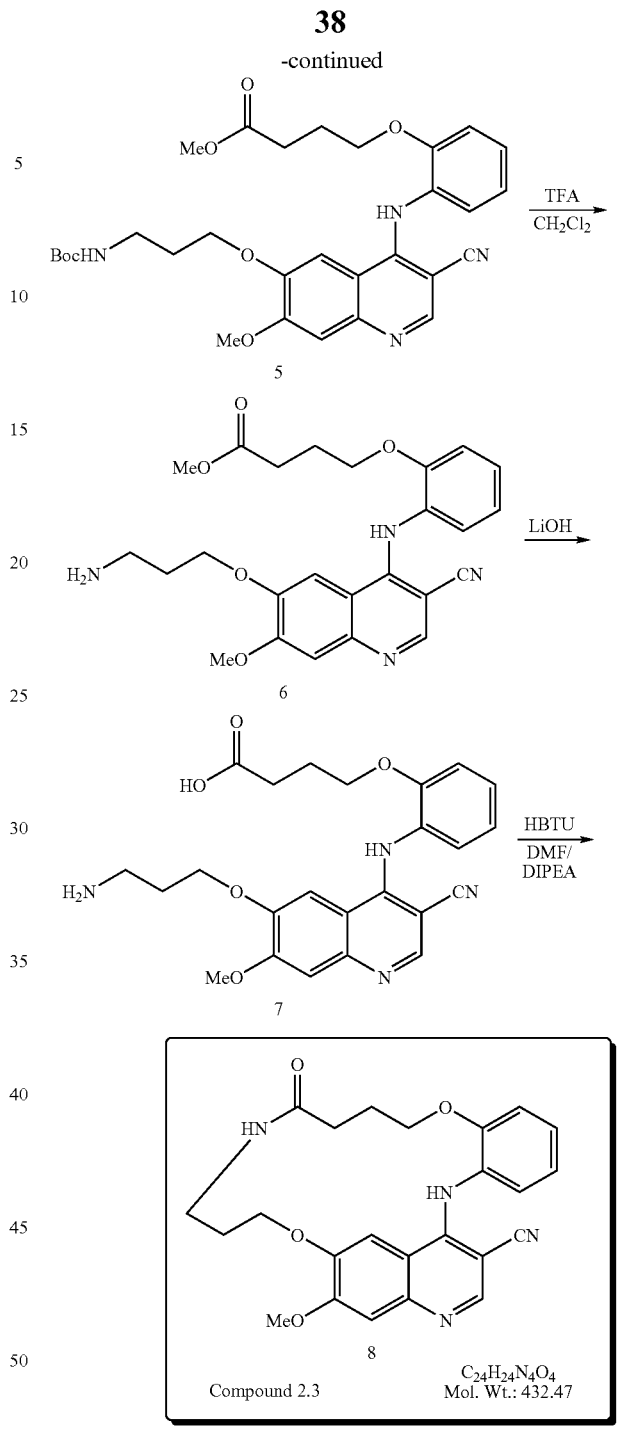

22-methoxy-14-oxo-11,12,13,14,15,16,17,18-octahydro-5H-1,20-(ethanediylidene)-pyrido[3,4-m][1,10,6,15]benzodioxadiazacycloheptadecine-4-carbonitrile (compound 2.3)

Nucleophilic Displacement

To a stirred suspension of chlorocyano quinoline 2 (1.05 equiv.) in iPrOH (11 mL/mmol), is added 1 (1 equiv.) followed by $Et_3N$ (1 equiv). The mixture is heated to reflux under $N_2$ atmosphere for 6 hours. The reaction mixture is evaporated to dryness and the resulting residue purified by flash-chromatography ($SiO_2$, AcOEt/Hexanes mixture) to afford pure 3.

Deacetylation.

Compound 3 is dissolved in MeOH/NH$_3$ 7N (8 mL/mmol). To this solution, iPrOH (2 mL/mmol) is added and the reaction mixture stirred at room temperature for 30-120 minutes (TLC monitoring). The mixture is concentrated to dryness and the resulting product used in the next step without further purification.

Alkylation Reaction.

To a stirred solution of 4 in DMF (5 mL/mmol), Cs$_2$CO$_3$ (3 equiv.) is added followed by the alkylating reagent (2.5 equiv.). The reaction mixture is stirred at room temperature overnight. The reaction mixture is partitioned between brine and AcOEt, and the layers separated. The organic layer is dried over MgSO$_4$, filtered and evaporated. The residue is purified by flash-chromatography (AcOEt/n-hexanes) to afford pure 5.

Cleavage of the Boc Group

To a cooled (0° C.) solution of 5 in CH$_2$Cl$_2$ (3 mL/mmol), TFA (2 mL/mmol) is added dropwise. The resulting mixture is allowed to warm to room temperature and stirred for 1-2 hours. A saturated solution of NaHCO$_3$ is added to the reaction mixture until basic pH is reached. The mixture is extracted with CH$_2$Cl$_2$ (2×). The combined organic layers are dried over MgSO$_4$, filtered and concentrated to dryness. The resulting free amine is obtained with enough purity to be used in the next step without further purification.

Saponification of the Ester Group

To a solution of 6 in MeOH/H$_2$O (10:1), LiOH.H$_2$O (5 equiv) is added and the reaction mixture is stirred at room temperature up to 2 hours. The solvent is evaporated under vaccuo and the residue is dissolved in DMF and filtered through a syntered glass funnel. The DMF is removed and the product used as such in the following reaction.

Cyclization Reaction

A solution of 7 (0.25 mmol, 1 equiv.) and DIPEA (6 equiv) in DMF (10 mL) is added dropwise to a solution of HBTU (3 equiv.) in DMF (100 mL/mmol of 7). The resulting mixture is stirred at room temperature for 1 hour. The solvent is evaporated and the product purified by reverse-phase HPLC.

Example O4

General Description for the Synthesis of Compounds of Formula 6

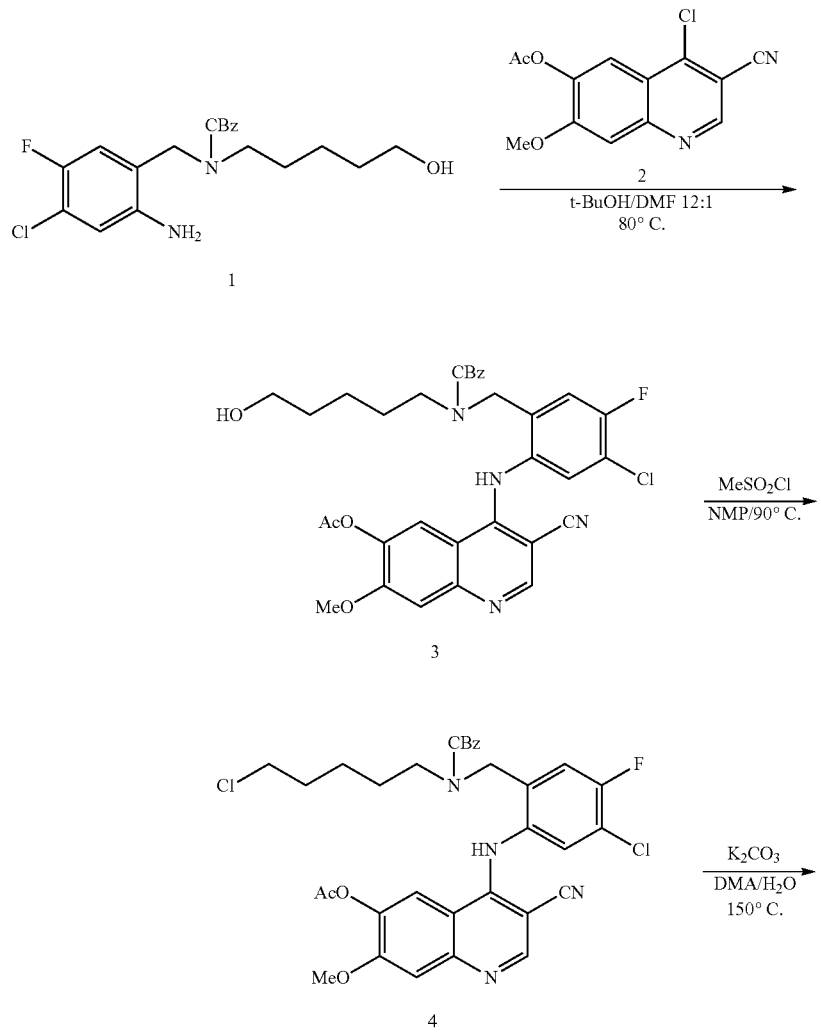

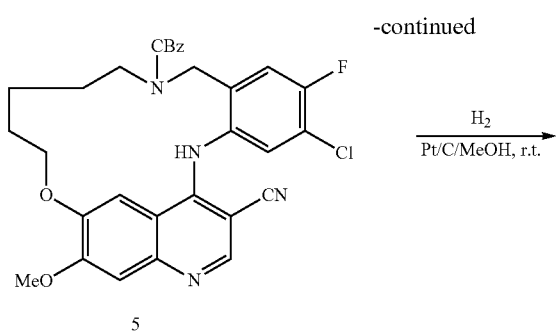
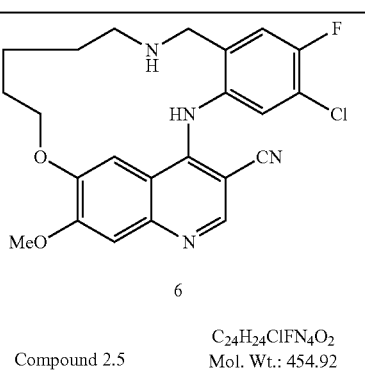

17-chloro-16-fluoro-20-methoxy-8,9,10,11,12,13,14,19-octahydro-4,6-(ethanediylidene)pyrido[4,3-b][6,1,12]benzoxadiazacyclopentadecine-1-carbonitrile (compound 2.5)

Nucleophilic Displacement

To a stirred solution of chlorocyano quinoline 2 (1.05 equiv.) in t-BuOH/DMF 12:1 (11 mL/mmol), 1 is added. The mixture is warmed to 80° C. under $N_2$ for 6 hours. The reaction mixture is evaporated to dryness and the resulting residue is stirred in MeCN for 1 hour. A solid precipitate is collected by filtration, washed with MeCN and dried to afford pure 3 in 63% yield.

Chlorination Reaction

Methyl sulfonyl chloride (9.4 mL) is added to a solution of 3 (12.50 mmol) in 50 mL of NMP at room temperature. The reaction mixture is then stirred at 90° C. for 1 hour. The reaction mixture is then poured out into 300 mL of $H_2O$, the aqueous layer extracted with AcOEt (3×100 mL). The combined organic layers are washed with $H_2O$ (2×100 mL), and finally the organic layer is dried, filtered and concentrated under reduced pressure. The resulting residue is purified by column chormatography affording pure 4 in 90% yield.

Cyclization Reaction

Compound 4 (5.0 mmol) and $K_2CO_3$ (5 equiv) are stirred in 83 mL of $DMA/H_2O$ (1:1) at 150° C. in a pre-heated sealed reactor for 30 minutes. The reaction mixture is concentrated under reduced pressure and the residue purified by reverse-phase HPLC to afford 5.

Removal of the CBz Group

To a solution of 5 (1 equiv) in MeOH (5 mL/mmol), Pt/C is added (10% w/w) and the resulting mixture is placed under $H_2$ atmosphere (balloon) and stirred at room temperature overnight (14 hours). The mixture is filtered through a short pad of celite and concentrated to dryness. The residue is purified by reverse-phase HPLC to afford pure 6.

Example O5

General Description for the Synthesis of Compounds of Formula 10

Scheme 13

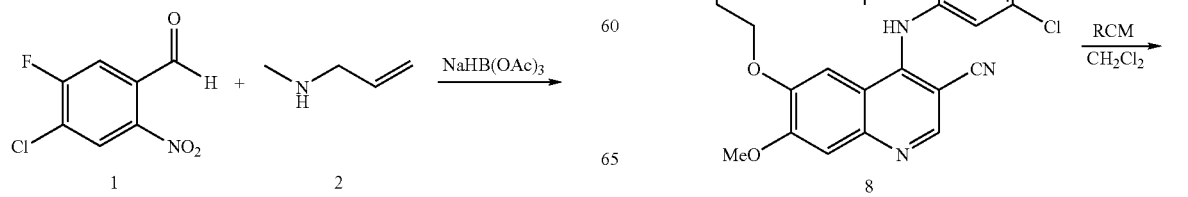

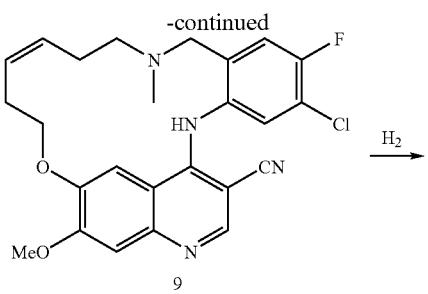

-continued

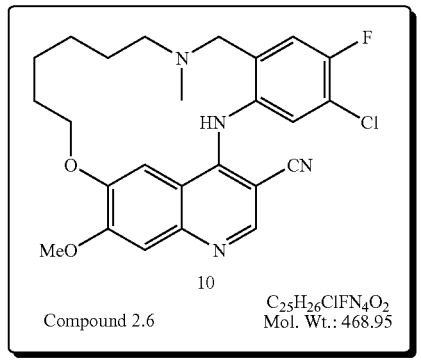 [SMILES: COc1cc2ncc(C#N)c3c2cc1OCCCCCCN(C)Cc1cc(F)c(Cl)cc1N3]

Compound 2.6
$C_{25}H_{26}ClFN_4O_2$
Mol. Wt.: 468.95

7-chloro-8-fluoro-21-methoxy-11-methyl-10,11,12,13,14,15,16,17-octahydro-5H-1,19-(ethanediylidene)pyrido[4,3-b][6,1,13]benzoxadiazacyclohexadecine-4-carbonitrile (compound 2.6)

Reductive Amination

To a solution of 1 (1 equiv.) and 2 (1 equiv.) in 1,2-dichloroethane (3 mL/mmol), MgSO$_4$ is added (1.5 equiv.) and the mixture stirred at room temperature for 90 minutes. To the resulting mixture NaBH(OAc)$_3$ (1.1 equiv.) is added in three portions (one portion per hour), and the resulting mixture stirred for additional 2 hours at room temperature. The reaction mixture is poured into a saturated solution of Na$_2$CO$_3$ and extracted with CH$_2$Cl$_2$ (3×). The combined organic layers are washed with brine, dried over MgSO$_4$, filtered and concentrated. The crude product is purified by flash chromatography (SiO$_2$, AcOEt/Hexanes mixture) to afford pure 3.

Reduction of the Nitro Group 5 equiv. of a 0.5 M solution of NH$_4$Cl in H$_2$O are added to a 0.1M solution of the nitro derivative 3 (1 equiv.) in toluene at room temperature. Iron powder (5 equiv.) are added while stirring vigorously. The reaction mixture is stirred at reflux temperature for 1 hour and then cooled to room temperature, filtered through a celite pad and the organic layer separated, dried over MgSO$_4$ and evaporated under reduced pressure. The aniline 4 is obtained quantitatively and is pure enough to be used in the next step without further purification.

Nucleophilic Displacement

To a stirred suspension of chlorocyano quinoline 5 (1.05 equiv.) in iPrOH (11 mL/mmol), 4 is added (1 equiv.). The mixture is allowed to react under reflux temperature under N$_2$ for 6-8 hours. The reaction mixture is evaporated to dryness and the resulting residue purified by flash-chromatography (SiO$_2$, AcOEt/Hexanes mixture) to afford pure 6.

Deacetylation

Compound 6 is dissolved in MeOH/NH$_3$ 7N (8 mL/mmol). To this solution, iPrOH (2 mL/mmol) is added and the reaction mixture stirred at room temperature for 30-120 minutes (TLC monitoring). The mixture is concentrated to dryness and the resulting product used in the next step without further purification.

Alkylation Reaction

To a stirred solution of 7 in DMF (5 mL/mmol), Cs$_2$CO$_3$ (3 equiv.) is added followed by the alkylating reagent (2.5 equiv.). The reaction mixture is stirred at room temperature overnight.

Ring Closing Metathesis

To a solution of 8 (1 equiv.) in anh. CH$_2$Cl$_2$ (100 mL/mmol), Grubbs's Catalyst second generation is added (20% mol). The resulting mixture is refluxed with stirring under N$_2$ atmosphere for 4 hours. After that time, additional catalyst (20% mol,) is added and the mixture is stirred for an additional 2 hours, by which time the reaction is essentially complete. The solvent is removed under reduced pressure and the resulting crude material is purified by flash-chromatography (AcOEt/hexanes) to yield pure product 9.

Hydrogenation of the Double Bond

To a solution of 9 (1 equiv.) in MeOH (5 mL/mmol), Pt/C is added (10% w/w) and the resulting mixture is placed under H$_2$ atmosphere (balloon) and stirred at room temperature overnight (14 hours). The mixture is filtered through a short pad of celite and concentrated to dryness. The residue is purified by reverse-phase HPLC to afford pure 10.

A. Preparation of the Intermediates

Example A1 a) Preparation of 1-pentanol, 5-[[(4-bromo-2-nitrophenyl)methyl]amino]- (intermediate 1)

A solution of 4-bromo-2-nitro-benzaldehyde, (0.013 mol), 5-amino-1-pentanol (0.013 mol) and titanium, tetrakis (2-propanolate) (0.014 mol) in ethanol (15 ml) was stirred at room temperature for 1 hour, then the reaction mixture was heated to 50° C. and stirred for 30 min. The mixture was cooled to room temperature and sodium hydroborate (0.013 mol) was added portionwise. The reaction mixture was stirred overnight and then poured out into ice water (50 ml). The resulting mixture was stirred for 20 min., the formed precipitate was filtered off (giving Filtrate (I)), washed with water and stirred in DCM (to dissolve the product and to remove it from the Ti-salt). The mixture was filtered and then the filtrate was dried (MgSO$_4$) and filtered, finally the solvent was evaporated dry. Filtrate (I) was evaporated until ethanol was removed and the aqueous concentrate was extracted 2 times with DCM. The organic layer was separated, dried (MgSO$_4$), filtered off and the solvent was evaporated dry, yielding 3.8 g (93%) of intermediate 1.

b) Preparation of carbamic acid, [(4-bromo-2-nitrophenyl)methyl](5-hydroxypentyl)-, 1,1-dimethylethyl ester (intermediate 2)

A solution of intermediate 1 (0.0032 mol) in DCM (20 ml) was stirred at room temperature and a solution of dicarbonic acid, bis(1,1-dimethylethyl)ester (0.0032 mol) in DCM (5 ml) was added dropwise. The reaction mixture was stirred for 1 hour at room temperature and washed 2 times with water. The organic layer was separated, dried (MgSO$_4$), filtered off and the solvent was evaporated dry, yielding intermediate 2.

c) Preparation of carbamic acid, [5-(acetyloxy)pentyl][(4-bromo-2-nitrophenyl)methyl]-, 1,1-dimethylethyl ester (intermediate 3)

A solution of intermediate 2 (0.0032 mol) and pyridine (0.032 mol) in acetic acid anhydride (15 ml) was stirred at room temperature for 16 hours, then the solvent was evaporated under reduced pressure and co-evaporated with toluene. The residue was used as such in the next reaction step, yielding 1.47 g (100%) of intermediate 3.

d) Preparation of carbamic acid, [5-(acetyloxy)pentyl][(2-amino-4-bromo-phenyl)-methyl]-, 1,1-dimethylethyl ester (intermediate 4)

A mixture of intermediate 3 (0.0033 mol) in THF (50 ml) was hydrogenated with Pt/C 5% (0.5 g) as a catalyst in the presence of thiophene solution (0.5 ml) After uptake of $H_2$ (3 equiv.), the catalyst was filtered off and the filtrate was evaporated, yielding intermediate 4.

Example A2 a) Preparation of benzoic acid, 2-amino-4-methoxy-5-(phenylmethoxy)-, methyl ester (intermediate 5)

A mixture of 4-methoxy-2-nitro-5-(phenylmethoxy)- benzoic acid, methylester, (0.166 mol) and triethylamine (0.198 mol) in THF (400 ml) was hydrogenated with Pt/C (5 g) as a catalyst in the presence of thiophene in DIPE (4 ml). After uptake of hydrogen (3 equivalents), the catalyst was filtered off and the filtrate was evaporated. The residue was treated with DIPE (300 ml) and stirred for 3 hours, then the resulting precipitate was filtered off and dried in a vacuum oven, yielding 45.9 g (96%) of intermediate 5.

b) Preparation of 3-quinolinecarbonitrile, 4-hydroxy-7-methoxy-6-(phenylmethoxy)- (intermediate 6)

A mixture of intermediate 5 (0.029 mol) and 1,1-dimethoxytrimethylamine, (0.058 mol) in DMF (30 ml) was stirred and refluxed for 2.5 hours, then the solvent was evaporated and co-evaporated with toluene (2×), giving Residue (I). A solution of n-BuLi, 2.5 M in hexane (0.058 mol) in THF (40 ml) was stirred and cooled to −75° C. and acetonitrile (0.058 mol) was added dropwise in 30 min. After 15 min. a solution of Residue (I) in THF (40 ml) was added dropwise and the reaction was quenched with acetic acid (0.058 mol) at −75° C., then the mixture was allowed to reach room temperature and was diluted with water (50 ml). The organic solvent (THF) was evaporated and the aqueous concentrate was diluted with 2-propanol (10 ml). This mixture was stirred for 1 hour and then the resulting precipitate was filtered and air-dried, yielding 4.4 g of intermediate 6. The filtrate was evaporated and then the residue was treated with water and DCM/MeOH (90/10). The resulting mixture was stirred for 15 minutes and the obtained solids were collected and air-dried, yielding 1.8 g of intermediate 6. Overall Yield: 6.2 g (70.4%).

c) Preparation of 3-quinolinecarbonitrile, 4,6-dihydroxy-7-methoxy- (intermediate 7)

A mixture of intermediate 6 (0.016 mol) in triethylamine (3 ml) and THF was hydrogenated with Pd/C (1.0 g) as a catalyst. After uptake of $H_2$ (1 equivalent), the catalyst was filtered off and the filtrate was evaporated, yielding 2.8 g of intermediate 7 (used as such in the next reaction step).

d) Preparation of 3-quinolinecarbonitrile, 6-(acetyloxy)-4-hydroxy-7-methoxy- (intermediate 8)

A mixture of intermediate 7 (0.011 mol) and pyridine (0.016 mol) in acetic anhydride (30 ml) was heated for 1 hour on an oil bath at 95° C., then the reaction mixture was allowed to reach room temperature and was stirred overnight. The solvent was evaporated and then the residue was treated with DIPE (30 ml) and the mixture was stirred for 2 hours. The resulting precipitate was collected and dried, yielding 2.58 g (90.8%) of intermediate 8.

e) Preparation of 3-quinolinecarbonitrile, 6-(acetyloxy)-4-chloro-7-methoxy- (intermediate 9)

A mixture of intermediate 8 (0.01 mol) and DMF (3 drops) in thionylchloride (25 ml) was heated for 2 hours on an oil bath at 80° C., then the solvent was evaporated. The residue was treated with DIPE and the mixture was stirred for 1 hour. The resulting solids were filtered off and air-dried. The residue (2.7 g) was dissolved in DCM and washed with $NaHCO_3$ solution. The organic layer was separated, dried ($MgSO_4$), filtered off and the solvent was evaporated, yielding 2.5 g of intermediate 9.

f) Preparation of carbamic acid, [[2-[[6-(acetyloxy)-3-cyano-7-methoxy-4-quinolinyl]amino]-4-bromophenyl]methyl][5-(acetyloxy)pentyl]-, 1,1-dimethylethyl ester (intermediate 10)

A mixture of intermediate 9 (0.0018 mol) and intermediate 4 (0.0018 mol) in 2-propanol (20 ml) was heated overnight on an oil bath at 65° C., then the solvent was evaporated. The residue was purified by column chromatography over silica gel (eluent: DCM/MeOH 99.7/0.3). One fraction was collected and the column was eluted again with DCM/MeOH/THF (90/5/5). Another fraction was collected and purified further by column chromatography over silica gel (eluent: DCM/MeOH gradient). The product fractions were collected and the solvent was evaporated, yielding 0.61 g (50.6%) of intermediate 10.

g) Preparation of carbamic acid, [[4-bromo-2-[(3-cyano-6-hydroxy-7-methoxy-4-quinolinyl)amino] phenyl]methyl](5-hydroxypentyl)-, 1,1-dimethylethyl ester (intermediate 11)

A stirring solution of intermediate 10 (0.000896 mol) in MeOH (20 ml) was treated with a solution of potassium carbonate (0.0018 mol) in water (5 ml). The reaction mixture was stirred overnight at room temperature and then neutralised with acetic acid until pH: 7. The solvent was evaporated. The residue was diluted with DCM and washed with water. The organic layer was separated, dried ($MgSO_4$), filtered off and the solvent was evaporate, yielding 0.38 g (73.1%) of intermediate 11, melting point 114.3-136.2° C.

B. Preparation of the Compounds

Example B1 a) Preparation of 4,6-ethanediylidenepyrido[4,3-b][6,1,12]benzoxadiazacyclopentadecine-13(8H)-carboxylic acid, 17-bromo-1-cyano-9,10,11,12,14,19-hexa-hydro-20-methoxy-, 1,1-dimethylethyl ester (compound 1)

A mixture of intermediate 11 (0.000649 mol) and ADDP (0.00094 mol) in THF p.a. (40 ml) was treated for 1 hour with tributylphosphine (0.00094 mol) and then extra ADDP (0.00094 mol) and tributylphosphine (0.00094 mol) were added. After 16 hours, the solvent was partially evaporated and the resulting concentrate was filtered and the filtrate evaporated. The residue was dissolved in THF p.a. (40 ml) and then ADDP (2 equivalents) was added, followed by tributylphosphine (2 equivalents). The resulting mixture was purified by reversed phase high-performance liquid chromatography. The product fractions were collected and the solvent was evaporated, yielding 0.0955 g (26.0%) of compound 1.

b) Preparation of 4,6-ethanediylidenepyrido[4,3-b][6,1,12]benzoxadiazacyclopentadecine-1-carbonitrile, 17-bromo-8,9,10,11,12,13,14,19-octahydro-20-methoxy-, monohydrochloride (compound 2)

A solution of compound 1 (0.00012 mol) in MeOH (5 ml) was treated with HCl/2-propanol (6N) (1 ml) and the reaction mixture was stirred over the weekend. The resulting precipitate was collected and dried an a vacuum oven, yielding 0.0197 g of compound 2, isolated as a monohydrochloric acid salt.

C. Pharmacological Examples

Example C.1

In vitro Inhibition of EGFR

The in vitro inhibition of EGFR was assessed using either the Flash Plate technology or the glass-fiber filter technology as described by Davies, S. P. et al., Biochem J. (2000), 351; p. 95-105. The Flash Plate technology is generally described by B. A. Brown et al. in High Throughput Screening (1997), p. 317-328. Editor(s): Devlin, John P. Publisher: Dekker, New York, N.Y.

In the Flash Plate EGFR kinase reaction assay, a kinase substrate consisting of biotinylated poly(L-glutamic acid-L-tyrosine) (poly(GT)biotin), is incubated with the aforementioned protein in the presence of ($^{33}$P) radiolabeled ATP. ($^{33}$P) phosphorylation of the substrate is subsequently measured as light energy emitted using a streptavidin-coated Flash Plate (PerkinElmer Life Sciences) by trapping and quantifying the binding of the biotin tagged and radiolabeled substrate.
Detailed Description The EGFR kinase reaction is performed at 30° C. for 60 minutes in a 96-well microtiter FlashPlate (PerkinElmer Life Sciences). For each of the tested compounds a full dose response $1.10^{-6}$M to $1.10^{-10}$M has been performed. IRESSA® and Tarceva™ (erlotinib) were used as reference compounds. The 100 µl reaction volume contains 54.5 mM TrisHCl pH 8.0, 10 mM MgCl$_2$, 100 µM Na$_3$VO$_4$, 5.0 µM unlabeled ATP, 1 mM DTT, 0.009% BSA, 0.8 µCi AT$^{33}$P, 0.35 µg/well poly(GT)biotin and 0.5 µg EGFR-kinase domain/well.

The reaction is stopped by aspirating the reaction mixture and washing the plate 3× with 200 µl wash/stop buffer (PBS+100 mM EDTA). After the final wash step 200 µl of wash/stop buffer was added to each well and the amount of phosphorylated ($^{33}$P) Poly(GT)biotin determined by counting (30 sec/well) in a microtiterplate scintillation counter.

In the glass-fiber filter technology EGFR kinase reaction assay, a kinase substrate consisting of poly(L-glutamic acid-L-tyrosine) (poly(GT)), is incubated with the aforementioned protein in the presence of ($^{33}$P) radiolabeled ATP. ($^{33}$P) Phosporylation of the substrate is subsequently measured as radioactivity bound on a glassfiber-filter.
Detailed Description The EGFR kinase reaction is performed at 25° C. for 10 minutes in a 96-well microtiterplate. For each of the tested compounds a full dose response $1.10^{-6}$M to $1.10^{-10}$M has been performed. IRESSA® and Tarceva™ (erlotinib) were used as reference compounds. The 25 µl reaction volume contains 60 mM TrisHCl pH 7.5, 3 mM MgCl$_2$, 3 mM Mn Cl$_2$, 3 µM Na$_3$VO$_4$, 50 µg/ml PEG20000, 5.0 µM unlabeled ATP, 1 mM DTT, 0.1 µCi AT$^{33}$P, 62.5 ng/well poly(GT) and 0.5 µg EGFR-kinase domain/well.

The reaction is stopped by adding 5 µl of a 3% phosphoric acid solution. 10 µl of the reaction mixture is then spotted onto a Filtermat A filter (Wallac) and washed 3 times for 5 min. in 75 mM phosphoric acid and 1 time for 5 min. in methanol prior to drying and quantification on the Typhoon (Amersham) using a LE phosphorage storage screen.

Example C.2

Serum Starved Proliferation Assay on the Ovarian Carcinoma SKOV3 Cells

The ovarian carcinoma cell line (SKOV3) was used in an epidermal growth factor stimulated cell proliferation assay, to assess the inhibitory effect of the compounds on EGF in whole cells.

In a first step the SKOV3 cells were incubated for 24 hours in the presence of 10% FCS serum. In the second step the cells were incubated with the compounds to be tested in a serum free condition (37° C. and 5% (v/v) CO$_2$) and subsequently stimulated for 72 hours with EGF at a final concentration of 100 ng/ml. The effect of the compounds on the EGF stimulation was finally assessed in a standard MTT cell viability assay.

The following table provides the pIC50 values of the compounds according to the invention, obtained using the above mentioned kinase assays.

| Compound number | FlashPlate. (C2): IC50 in nM | SKOV3 cell (C3): IC50 in µM |
|---|---|---|
| 2 | 8.3 | 6.8 |

D. Composition Examples

The following formulations exemplify typical pharmaceutical compositions suitable for systemic administration to animal and human subjects in accordance with the present invention.

"Active ingredient" (A.I.) as used throughout these examples relates to a compound of formula (I) or a pharmaceutically acceptable addition salt thereof.

Example D.1

Film-coated Tablets

Preparation of Tablet Core

A mixture of A.I. (100 g), lactose (570 g) and starch (200 g) was mixed well and thereafter humidified with a solution of sodium dodecyl sulfate (5 g) and polyvinyl-pyrrolidone (10 g) in about 200 ml of water. The wet powder mixture was sieved, dried and sieved again. Then there was added microcrystalline cellulose (100 g) and hydrogenated vegetable oil (15 g). The whole was mixed well and compressed into tablets, giving 10.000 tablets, each comprising 10 mg of the active ingredient.

Coating

To a solution of methyl cellulose (10 g) in denaturated ethanol (75 ml) there was added a solution of ethyl cellulose (5 g) in $CH_2Cl_2$ (150 ml). Then there were added $CH_2Cl_2$ (75 ml) and 1,2,3-propanetriol (2.5 ml). Polyethylene glycol (10 g) was molten and dissolved in dichloromethane (75 ml). The latter solution was added to the former and then there were added magnesium octadecanoate (2.5 g), polyvinyl-pyrrolidone (5 g) and concentrated color suspension (30 ml) and the whole was homogenated. The tablet cores were coated with the thus obtained mixture in a coating apparatus.

The invention claimed is:

1. A compound having the formula

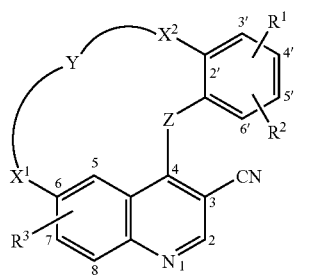

the N-oxide forms, the pharmaceutically acceptable addition salts and the stereochemically isomeric forms thereof, wherein Z represents O, NH or S;

Y represents —$C_{3-9}$alkyl-, —$C_{3-9}$alkenyl-, —$C_{1-5}$alkyl-oxy-$C_{1-5}$alkyl-, —$C_{1-5}$alkyl-$NR^{12}$—$C_{1-5}$alkyl-, —$C_{1-5}$alkyl-$NR^{13}$—CO—$C_{1-5}$alkyl-, —$C_{1-5}$alkyl-CO—$NR^{14}$—$C_{1-5}$alkyl-, —$C_{1-6}$alkyl-CO—NH—, —$C_{1-6}$alkyl-NH—CO—, —CO—NH—$C_{1-6}$alkyl-, —NH—CO—$C_{1-6}$alkyl-, —CO—$C_{1-7}$alkyl-, —$C_{1-7}$alkyl-CO—, $C_{1-6}$alkyl-CO—$C_{1-6}$alkyl, —$C_{1-2}$alkyl-NH—CO—$CH_2R^{15}$—NH—;

$X^1$ represents a direct bond, O, —O—$C_{1-2}$alkyl-, CO, —CO—$C_{1-2}$alkyl-, $NR^{10}$, —$NR^{10}$—$C_{1-2}$alkyl-, $NR^{16}$—CO—, $NR^{16}$—CO—$C_{1-2}$alkyl, —O—N═CH— or $C_{1-2}$alkyl;

$X^2$ represents a direct bond, O, —O—$C_{1-2}$alkyl-, CO, —CO—$C_{1-2}$alkyl-, $NR^{11}$, $NR^{11}$—$C_{1-2}$alkyl-, $NR^{17}$—CO—, $NR^{17}$—CO—$C_{1-2}$alkyl, $Het^{20}$—$C_{1-2}$alkyl, —O—N═CH— or $C_{1-2}$alkyl;

$R^1$ represents hydrogen, cyano, halo, hydroxy, formyl, $C_{1-6}$alkoxy-, $C_{1-6}$alkyl-, $C_{1-6}$alkoxy- substituted with halo, $C_{1-4}$alkyl substituted with one or where possible two or more substituents selected from hydroxy or halo;

$R^2$ represents hydrogen, cyano, halo, hydroxy, hydroxycarbonyl-, $Het^{16}$-carbonyl-, $C_{1-4}$alkyloxycarbonyl-, $C_{1-4}$alkylcarbonyl-, aminocarbonyl-, mono-or di($C_{1-4}$alkyl)aminocarbonyl-, $Het^1$, formyl, $C_{1-4}$alkyl-, $C_{2-6}$alkynyl-, $C_{3-6}$cycloalkyl-, $C_{3-6}$cycloalkyloxy-, $C_{1-6}$alkoxy-, $Ar^5$, $Ar^1$-oxy-, dihydroxyborane , $C_{1-6}$alkoxy- substituted with halo, $C_{1-4}$alkyl substituted with one or where possible two or more substituents selected from halo, hydroxy or $NR^4R^5$, $C_{1-4}$alkylcarbonyl- wherein said $C_{1-4}$alkyl is optionally substituted with one or where possible two or more substituents selected from hydroxy or $C_{1-4}$alkyl-oxy-;

$R^3$ represents hydrogen, hydroxy, $Ar^3$-oxy, $Ar^4$—$C_{1-4}$alkyloxy-, $C_{1-4}$alkyloxy-, $C_{2-4}$alkenyloxy- optionally substituted with $Het^{12}$ or $R^3$ represents $C_{1-4}$alkyloxy substituted with one or where possible two or more substituents selected from $C_{1-4}$alkyloxy-, hydroxy, halo, $Het^2$-, —$NR^6R^7$, -carbonyl- $NR^8R^9$ or $Het^3$-carbonyl-;

$R^4$ and $R^5$ are each independently selected from hydrogen or $C_{1-4}$alkyl;

$R^6$ and $R^7$ are each independently selected from hydrogen, $C_{1-4}$alkyl, $Het^8$, aminosulfonyl-, mono- or di ($C_{1-4}$alkyl)-aminosulfonyl, hydroxy-$C_{1-4}$alkyl-, $C_{1-4}$alkyl-oxy-$C_{1-4}$alkyl-, hydroxycarbonyl-$C_{1-4}$alkyl-, $C_{3-6}$cycloalkyl, $Het^9$-carbonyl-$C_{1-4}$alkyl-, $Het^{10}$-carbonyl-, polyhydroxy-$C_{1-4}$alkyl-, $Het^{11}$-$C_{1-4}$alkyl- or $Ar^2$—$C_{1-4}$alkyl-;

$R^8$ and $R^9$ are each independently selected from hydrogen, $C_{1-4}$alkyl, $C_{3-6}$cycloalkyl, $Het^4$, hydroxy-$C_{1-4}$alkyl-$C_{1-4}$alkyloxy- or polyhydroxy-$C_{1-4}$alkyl-;

$R^{10}$ represents hydrogen, $C_{1-4}$alkyl, $Het^5$, $Het^6$-$C_{1-4}$alkyl-, $C_{2-4}$alkenylcarbonyl- optionally substituted with $Het^7$-$C_{1-4}$alkylaminocarbonyl-, $C_{2-4}$alkenylsulfonyl-, $C_{1-4}$alkyloxy$C_{1-4}$alkyl- or phenyl optionally substituted with one or where possible two or more substituents selected from hydrogen, hydroxy, amino or $C_{1-4}$alkyloxy-;

$R^{11}$ represents hydrogen, $C_{1-4}$alkyl, $C_{1-4}$alkyl-oxy-carbonyl-, $Het^{17}$, $Het^{18}$-$C_{1-4}$alkyl-, $C_{2-4}$alkenylcarbonyl- optionally substituted with $Het^{19}$-$C_{1-4}$alkylaminocarbonyl-, $C_{2-4}$alkenylsulfonyl-, $C_{1-4}$alkyloxy$C_{1-4}$alkyl- or phenyl optionally substituted with one or where possible two or more substituents selected from hydrogen, hydroxy, amino or $C_{1-4}$alkyloxy-;

$R^{12}$ represents hydrogen, $C_{1-4}$alkyl, $Het^{13}$, $Het^{14}$-$C_{1-4}$alkyl- or phenyl optionally substituted with one or where possible two or more substituents selected from hydrogen, hydroxy, amino or $C_{1-4}$alkyloxy-;

$R^{13}$ and $R^{14}$ are each independently selected from hydrogen, $C_{1-4}$alkyl, $Het^{15}$-$C_{1-4}$alkyl- or $C_{1-4}$alkyloxy$C_{1-4}$alkyl-;

$R^{15}$ represents hydrogen or $C_{1-4}$alkyl optionally substituted with phenyl, indolyl, methylsulfide, hydroxy, thiol, hydroxyphenyl, aminocarbonyl, hydroxycarbonyl, amine, imidazoyl or guanidino;

$R^{16}$ and $R^{17}$ are each independently selected from hydrogen, $C_{1-4}$alkyl, $Het^{21}$-$C_{1-4}$alkyl or $C_{1-4}$alkyloxy$C_{1-4}$alkyl;

$Het^1$ represents a heterocycle selected from piperidinyl, morpholinyl, piperazinyl, furanyl, pyrazolyl, dioxolanyl, thiazolyl, oxazolyl, imidazolyl, isoxazolyl, oxadiazolyl, pyridinyl or pyrrolidinyl wherein said $Het^1$ is optionally substituted amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl- mono- or di($C_{1-4}$alkyl)amino- or amino-carbonyl-;

$Het^2$ represents a heterocycle selected from morpholinyl, piperazinyl, piperidinyl, pyrrolidinyl, thiomorpholinyl or dithianyl wherein said $Het^2$ is optionally substituted with one or where possible two or more substituents selected from hydroxy, halo, amino, $C_{1-4}$alkyl-, hydroxy-$C_{1-4}$alkyl-, $C_{1-4}$alkyl-oxy-$C_{1-4}$alkyl-, hydroxy-$C_{1-4}$alkyl-oxy-$C_{1-4}$alkyl-, mono- or di($C_{1-4}$alkyl)amino-, mono- or di($C_{1-4}$alkyl)amino-$C_{1-4}$alkyl-, amino$C_{1-4}$alkyl-, mono- or di($C_{1-4}$alkyl)amino-sulfonyl-, aminosulfonyl-;

$Het^3$, $Het^4$ and $Het^8$ each independently represent a heterocycle selected from morpholinyl, piperazinyl, piperidinyl, furanyl, pyrazolyl, dioxolanyl, thiazolyl, oxazolyl, imidazolyl, isoxazolyl, oxadiazolyl, pyridinyl or pyrrolidinyl wherein said $Het^3$, $Het^4$ or $Het^8$ is optionally substituted with one or where possible two or more substituents selected from hydroxy-, amino-, $C_{1-4}$alkyl-, $C_{3-6}$cycloalkyl-$C_{1-4}$alkyl-, aminosulfonyl-, mono- or di($C_{1-4}$alkyl)aminosulfonyl or amino-$C_{1-4}$alkyl-;

$Het^5$ represent a heterocycle selected from pyrrolidinyl or piperidinyl wherein said $Het^5$ optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^6$ and $Het^7$ each independently represent a heterocycle selected from morpholinyl, pyrrolidinyl, piperazinyl or piperidinyl wherein said $Het^6$ and $Het^7$ are optionally substituted with one or where possible two or more substituents selected from $C_{1-4}$alkyl, $C_{3-6}$cycloalkyl, hydroxy-$C_{1-4}$alkyl-, $C_{1-4}$alkyloxy-$C_{1-4}$alkyl- or polyhydroxy-$C_{1-4}$alkyl-;

$Het^9$ and $Het^{10}$ each independently represent a heterocycle selected from furanyl, piperidinyl, morpholinyl, piperazinyl, pyrazolyl, dioxolanyl, thiazolyl, oxazolyl, imidazolyl, isoxazolyl, oxadiazolyl, pyridinyl or pyrrolidinyl wherein said $Het^9$ or $Het^{10}$ is optionally substituted $C_{1-4}$alkyl, $C_{3-6}$cycloalkyl-$C_{1-4}$alkyl- or amino-$C_{1-4}$alkyl-;

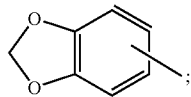

$Het^{11}$ represents a heterocycle selected from indolyl or $Het^{12}$ represents a heterocycle selected from morpholinyl, piperazinyl, piperidinyl, pyrrolidinyl, thiomorpholinyl or dithianyl wherein said $Het^{12}$ is optionally substituted with one or where possible two or more substituents selected from hydroxy, halo, amino, $C_{1-4}$alkyl-, hydroxy-$C_{1-4}$alkyl-, $C_{1-4}$alkyl-oxy-$C_{1-4}$alkyl-, hydroxy-$C_{1-4}$alkyl-oxy-$C_{1-4}$alkyl-, mono- or di($C_{1-4}$alkyl)amino- or mono- or di($C_{1-4}$alkyl)amino-$C_{1-4}$alkyl-;

$Het^{13}$ represent a heterocycle selected from pyrrolidinyl or piperidinyl wherein said $Het^{13}$ is optionally substituted with one or where possible two or more substituents selected from $C_{1-4}$alkyl, $C_{3-6}$cycloalkyl, hydroxy-$C_{1-4}$allkyl-, $C_{1-4}$alkyloxy$C_{1-4}$alkyl or polyhydroxy-$C_{1-4}$alkyl-;

$Het^{14}$ represent a heterocycle selected from morpholinyl, pyrrolidinyl, piperazinyl or piperidinyl wherein said $Het^{14}$ is optionally substituted with one or where possible two or more substituents selected from $C_{1-4}$alkyl, $C_{3-6}$cycloalkyl, hydroxy-$C_{1-4}$allkyl-, $C_{1-4}$alkyloxy $C_{1-4}$alkyl or polyhydroxy-$C_{1-4}$alkyl-;

$Het^{15}$ and $Het^{21}$ each independently represent a heterocycle selected from morpholinyl, pyrrolidinyl, piperazinyl or piperidinyl wherein said heterocycles are optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{16}$ represent a heterocycle selected from morpholinyl, pyrrolidinyl, piperazinyl, 1,3,2-dioxaborolane or piperidinyl wherein said heterocycle is optionally substituted with one or more substituents selected from $C_{1-4}$alkyl; and $Het^{17}$ represent a heterocycle selected from pyrrolidinyl or piperidinyl wherein said $Het^{17}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{18}$ and $Het^{19}$ each independently represent a heterocycle selected from morpholinyl, pyrrolidinyl, piperazinyl or piperidinyl wherein said $Het^{18}$ and $Het^{19}$ are optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{20}$ represents a heterocycle selected from pyrrolidinyl, 2-pyrrolidinyl, piperidinyl, piperazinyl, morpholinyl, imidazolyl or pyrazolidinyl wherein said $Het^{20}$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-; and $Ar^1$, $Ar^2$ $Ar^3$, $Ar^4$ and $Ar^5$ each independently represent phenyl optionally substituted with cyano, $C_{1-4}$alkylsulfonyl-, $C_{1-4}$alkylsulfonylamino-, aminosulfonylamino-, hydroxy-$C_{1-4}$alkyl, aminosulfonyl-, hydroxy-, $C_{1-4}$alkyloxy- or $C_{1-4}$alkyl.

2. A compound according to claim 1 wherein;

Z represents NH;

Y represents —$C_{3-9}$alkyl-, —$C_{2-9}$alkenyl-, —$C_{1-5}$alkyl-oxy-$C_{1-5}$alkyl-, —$C_{1-5}$alkyl-$NR^{12}$—$C_{1-5}$alkyl-, —$C_{1-5}$alkyl-$NR^{13}$—CO—$C_{1-5}$alkyl-, —$C_{1-6}$alkyl-NH—CO—, —CO—$C_{1-7}$alkyl-, —$C_{1-7}$alkyl-CO— or $C_{1-6}$alkyl-CO—$C_{1-6}$alkyl;

$X^1$ represents O, —O—$C_{1-2}$alkyl-, —O—N=CH—, $NR^{16}$—CO, —$NR^{16}$—CO—$C_{1-2}$alkyl-, $NR^{10}$ or —$NR^{10}$—$C_{1-2}$alkyl-;

$X^2$ represents a direct bond, O, —O—$C_{1-2}$alkyl-, —O—N=CH—, $Het^{20}$-$C_{1-2}$alkyl, $C_{1-2}$alkyl, $NR^{17}$—CO, —$NR^{17}$—CO—$C_{1-2}$alkyl-, $NR^{11}$ or $NR^{11}$—$C_{1-2}$alkyl-;

$R^1$ represents hydrogen, cyano, halo or hydroxy;

$R^2$ represents hydrogen, cyano, halo, hydroxy, hydroxycarbonyl-, $C_{1-4}$alkyloxycarbonyl-, $Het^{16}$-carbonyl-, $C_{2-6}$alkynyl-, $Ar^5$ or $Het^1$;

$R^3$ represents hydrogen, hydroxy, $C_{1-4}$alkyloxy-, $Ar^4$—$C_{1-4}$alkyloxy or $R^3$ represents $C_{1-4}$alkyloxy substituted with one or where possible two or more substituents selected from $C_{1-4}$alkyloxy-or $Het^2$-;

$R^{10}$ represents hydrogen, $C_{1-4}$alkyl- or $C_{1-4}$alkyl-oxy-carbonyl-;

$R^{11}$ represents hydrogen, $C_{1-4}$alkyl- or $C_{1-4}$alkyl-oxy-carbonyl-;

$R^{12}$ represents $Het^{14}$-$C_{1-4}$alkyl;

$R^{16}$ represents hydrogen, $C_{1-4}$alkyl-, $Het^{21}$-$C_{1-4}$alkyl or $C_{1-4}$alkyl-oxy-$C_{1-4}$alkyl;

$R^{17}$ represents hydrogen, $C_{1-4}$alkyl-, $Het^{21}$-$C_{1-4}$alkyl or $C_{1-4}$alkyl-oxy-$C_{1-4}$alkyl;

$Het^1$ represents thiazolyl optionally substituted amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl- mono- or di($C_{1-4}$alkyl)amino- or amino-carbonyl-;

$Het^2$ represents a heterocycle selected from morpholinyl, piperazinyl, piperidinyl or pyrrolidinyl wherein said $Het^2$ is optionally substituted with one or where possible two or more substituents selected from hydroxy, amino or $C_{1-4}$alkyl-;

$Het^{14}$ represents a heterocycle selected from morpholinyl, piperazinyl, piperidinyl or pyrrolidinyl wherein said Het$^{14}$ is optionally substituted with one or where possible two or more substituents selected from hydroxy, amino or C$_{1-4}$alkyl-;

Het$^{16}$ represents a heterocycle selected from piperidinyl, morpholinyl or pyrrolidinyl;

Het$^{20}$ represents a heterocycle selected from pyrrolidinyl, 2-pyrrolidinyl or piperidinyl;

Het$^{21}$ represents a heterocycle selected from morpholinyl, piperazinyl, piperidinyl or pyrrolidinyl wherein said Het$^{21}$ is optionally substituted with one or where possible two or more substituents selected from hydroxy, amino or C$_{1-4}$alkyl-;

Ar$^{4}$ represents phenyl optionally substituted with cyano, hydroxy-, C$_{1-4}$alkyloxy or C$_{1-4}$alkyl;

Ar$^{5}$ represents phenyl optionally substituted with cyano, hydroxy, C$_{1-4}$alkyloxy or C$_{1-4}$alkyl.

3. A compound according to claim 1 wherein;

Z represents NH;

Y represents —C$_{3-9}$alkyl-, —C$_{1-5}$alkyl-NR$^{12}$—C$_{1-5}$alkyl-, —C$_{1-5}$alkyl-NR$^{13}$—CO—C$_{1-5}$alkyl-, —C$_{1-6}$alkyl-NH—CO— or —CO—NH —C$_{1-6}$alkyl-;

X$^{1}$ represents a direct bond, NW$^{10}$, —NR$^{10}$—C$_{1-2}$alkyl-, —NR—CH$_{2}$—, —C$_{1-2}$alkyl-, —O—C$_{1-2}$alkyl, —O— or —O—CH$_{2}$—;

X$^{2}$ represents a-O—, NR$^{11}$, NR$^{17}$—CO, NR$^{17}$—CO—C$_{1-2}$alkyl or Het$^{20}$-C$_{1-2}$alkyl;

R$^{1}$ represents hydrogen or halo;

R$^{2}$ represents hydrogen, cyano, halo, hydroxycarbonyl-, C$_{1-4}$alkyloxycarbonyl-, Het$^{16}$-carbonyl- or Ar$^{5}$;

R$^{3}$ represents hydrogen, hydroxy, C$_{1-4}$alkyloxy-, Ar$^{4}$—C$_{1-4}$alkyloxy or R$^{3}$ represents C$_{1-4}$alkyloxy substituted with one or where possible two or more substituents selected from C$_{1-4}$alkyloxy- or Het$^{2}$-;

R$^{10}$ represents hydrogen;

R$^{11}$ represents hydrogen, C$_{1}$ alkyl- or C$_{1-4}$alkyl-oxy-carbonyl-;

R$^{12}$ represents Het$^{14}$-C$_{1-4}$alkyl;

R$^{13}$ represents hydrogen;

R$^{17}$ represents hydrogen;

Het$^{2}$ represents a heterocycle selected from morpholinyl, piperazinyl, piperidinyl or pyrrolidinyl wherein said Het$^{2}$ is optionally substituted with one or where possible two or more substituents selected from hydroxy, amino or C$_{1-4}$alkyl-;

Het$^{14}$ represents morpholinyl;

Het$^{16}$ represents a heterocycle selected from morpholinyl or pyrrolidinyl;

Het$^{20}$ represents pyrrolidinyl or piperidinyl;

Ar$^{4}$ represents phenyl;

Ar$^{5}$ represents phenyl optionally substituted with cyano.

4. A compound according to claim 1, wherein the R$^{1}$ substituent is at position 4', the R$^{2}$ substituent is at position 5' and the R$^{3}$ substituent at position 7 of the structure of formula (I).

5. A pharmaceutical composition comprising a pharmaceutically acceptable carrier and, as active ingredient, an effective kinase inhibitory amount of a compound as described in claim 1.

6. A method of treating ovarian cancer, the method comprising administering to an animal in need of such treatment a therapeutically effective amount of a compound as claimed in claim 1.

* * * * *